(12) United States Patent
Brikman et al.

(10) Patent No.: US 12,144,509 B2
(45) Date of Patent: Nov. 19, 2024

(54) TOURNIQUET

(71) Applicant: M.A.S. MED GLOBAL LTD, Rosh Haayin (IL)

(72) Inventors: Tzach-Yitzhak Brikman, Kfar Verburg (IL); Menashe Shaked, Kfar Verburg (IL); Derek Ryden, Gloucestershire (GB)

(73) Assignee: MAS Med Global Ltd, Rosh Haayin (IL)

( * ) Notice: Subject to any disclaimer, the term of this patent is extended or adjusted under 35 U.S.C. 154(b) by 764 days.

(21) Appl. No.: 17/238,669

(22) Filed: Apr. 23, 2021

(65) Prior Publication Data
US 2021/0236141 A1    Aug. 5, 2021

Related U.S. Application Data

(63) Continuation-in-part of application No. PCT/IL2019/051154, filed on Oct. 24, 2019.

(30) Foreign Application Priority Data

Oct. 25, 2018 (IL) .......................................... 262623

(51) Int. Cl.
*A61B 17/135* (2006.01)
*A61B 17/00* (2006.01)
*A61B 17/12* (2006.01)

(52) U.S. Cl.
CPC .. *A61B 17/135* (2013.01); *A61B 2017/00548* (2013.01); *A61B 2017/00557* (2013.01); *A61B 2017/12004* (2013.01)

(58) Field of Classification Search
CPC ........ A61B 17/135; A61B 2017/00548; A61B 2017/00557; A61B 2017/12004;
(Continued)

(56) References Cited

U.S. PATENT DOCUMENTS

| | | | | |
|---|---|---|---|---|
| 1,269,620 A | * | 6/1918 | Levine | A61B 17/135 600/499 |
| 2,031,870 A | * | 2/1936 | Vertuno | A61B 17/135 606/202 |

(Continued)

FOREIGN PATENT DOCUMENTS

| | | |
|---|---|---|
| GB | 2278911 | 12/1994 |
| WO | 2014023960 A1 | 2/2014 |
| WO | 2014191987 A1 | 12/2014 |

OTHER PUBLICATIONS

Delfi Medical Elastic Cuff online brochure: http://www.delfimedical. com/wp-content/uploads/2013/10/EasifitCuffBrochure-Sept2013. pdfJun. 10, 2017 (publication was dated according to a search on Internet Archive: https://web.archive.org/web/20170101000000*/ http:/www.delfimedical.com/wp-content/uploads/2013/10/ EasifitCuffBrochure-Sep2013.pdf) Delfi Medical Jun. 10, 2017.
(Continued)

*Primary Examiner* — Tan-Uyen T Ho
*Assistant Examiner* — Osama Nemer

(57) ABSTRACT

A pneumatic tourniquet has a constricting device that comprises a rocker, such that when the rocker is angularly displaced by contact with a wounded limb, a clamping force is applied by a rocker surface and a clamping edge onto a sealing element to prevent flow of the pressurized gas from an interposed inflated strap to a free end, causing the strap free end to be considerably thinner than the main strap section. In one embodiment, a gas flow control assembly comprises a casing containing a force transmitting element and a gas cartridge; and a pivotable activation handle, wherein, upon pivoted displacement of the activation handle, pressurized gas is caused to be discharged from the gas cartridge and flow to an interior of the strap. In other embodiments, the pneumatic tourniquet comprises one or
(Continued)

more of a flow control unit, a manual pressure release initiator, and a puncture mitigating connection section.

16 Claims, 29 Drawing Sheets

(58) Field of Classification Search
CPC ........ A61B 17/1327; A61B 2090/0807; A61B 17/132; A61B 17/1322; A61B 17/1325; A61B 17/1355
See application file for complete search history.

(56) References Cited

U.S. PATENT DOCUMENTS

| | | | | |
|---|---|---|---|---|
| 2,839,062 A * | 6/1958 | Jordan | ................ | A61B 17/135 606/202 |
| 3,670,735 A | 6/1972 | Hazlewood | | |
| 3,756,239 A * | 9/1973 | Smythe | ................ | A61B 17/135 600/499 |
| 4,637,394 A * | 1/1987 | Racz | ................ | A61B 17/135 606/202 |
| 5,234,459 A * | 8/1993 | Lee | ................ | A61B 17/135 606/202 |
| 5,741,295 A * | 4/1998 | McEwen | ................ | A61B 17/135 606/202 |
| 6,659,938 B1 * | 12/2003 | Orlowski | ................ | A61F 5/41 600/38 |
| 6,682,547 B2 | 1/2004 | McEwen et al. | | |
| 6,746,406 B2 * | 6/2004 | Lia | ................ | A61B 5/02233 600/499 |
| 6,746,470 B2 * | 6/2004 | McEwen | ................ | A61B 17/135 606/202 |
| 8,568,441 B2 | 10/2013 | McEwen et al. | | |
| 9,439,827 B2 * | 9/2016 | Saatchi | ................ | A61H 1/006 |
| 10,517,606 B1 * | 12/2019 | Donaldson | ................ | A61M 5/158 |
| 10,555,741 B1 * | 2/2020 | Croushorn | ................ | A61B 17/1325 |
| 2003/0139766 A1 * | 7/2003 | McEwen | ................ | A61B 17/135 606/202 |
| 2007/0191881 A1 | 8/2007 | Amisar et al. | | |
| 2007/0244506 A1 * | 10/2007 | McEwen | ................ | A61B 17/135 606/202 |
| 2015/0032149 A1 * | 1/2015 | Croushorn | ................ | A61B 17/135 606/202 |
| 2015/0230803 A1 | 8/2015 | Schreckengaust et al. | | |

OTHER PUBLICATIONS

Estebe, J.P. et al., "Tourniquet pain in a volunteer study: efffect of changes in cuff width and pressure", Anaesthesia, 2000, 55; pp. 21-26.

International Search Report for International Application No. PCT/IL2019/051154; International Filing Date: Oct. 24, 2019; Date of mailing: Mar. 17, 2020; 8 pages.

Written Opinion of the International Searching Authority for International Application No. PCT/IL2019/051154; International Filing Date: Oct. 24, 2019; Date of mailing: Mar. 17, 2020; 11 pages.

* cited by examiner

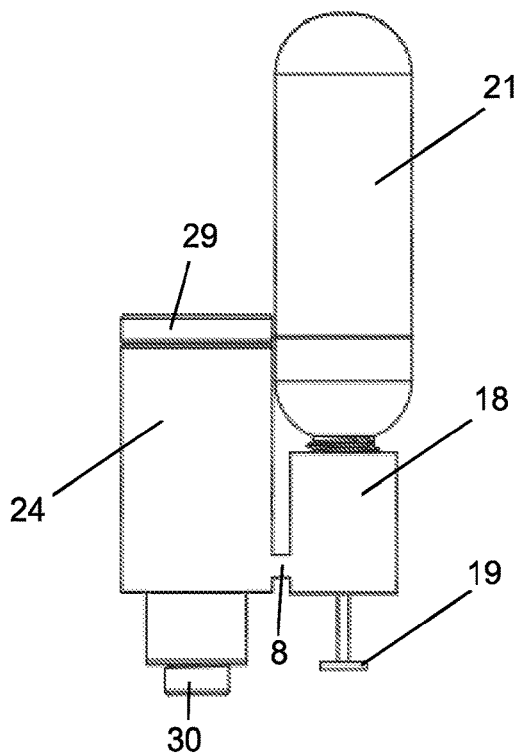
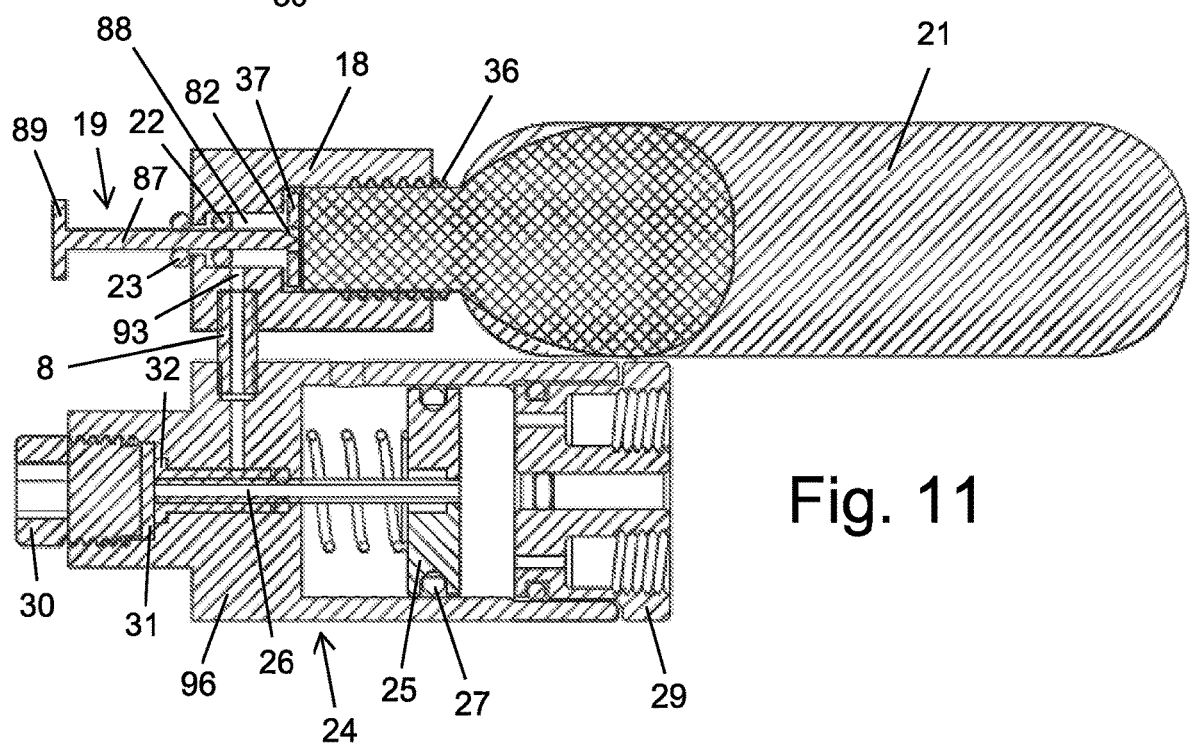

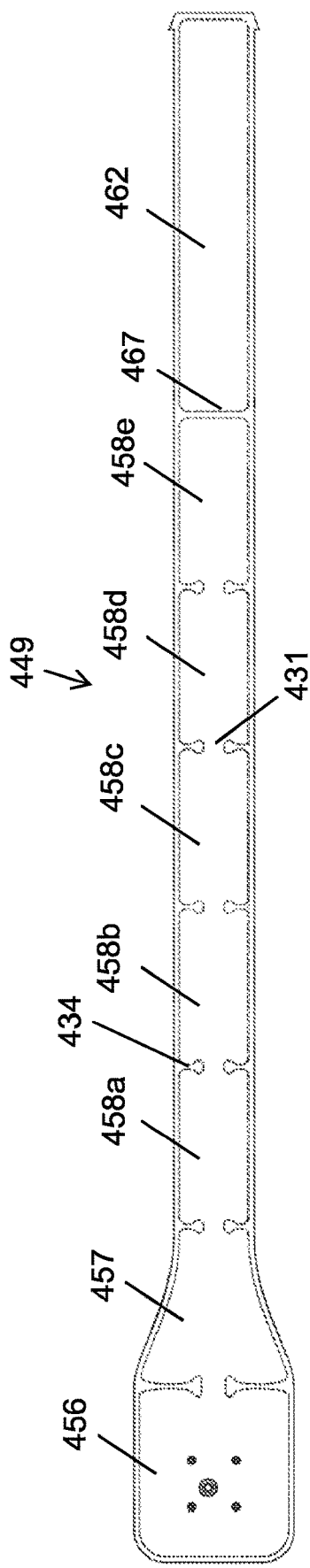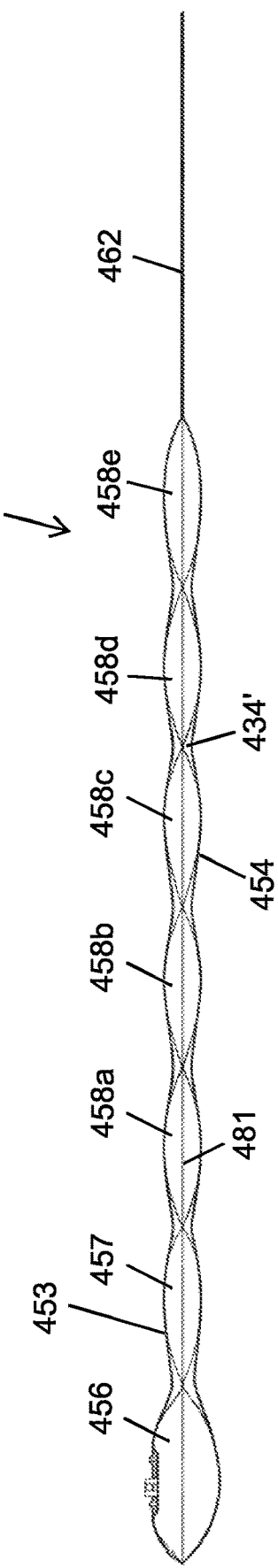

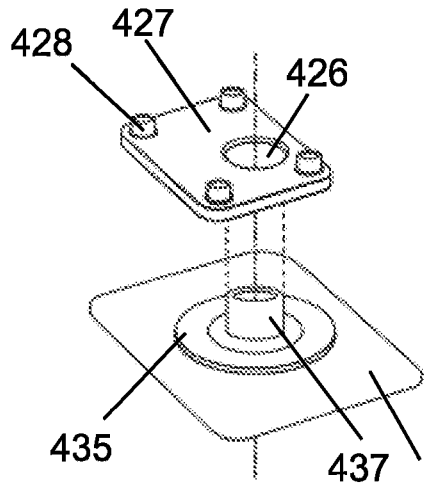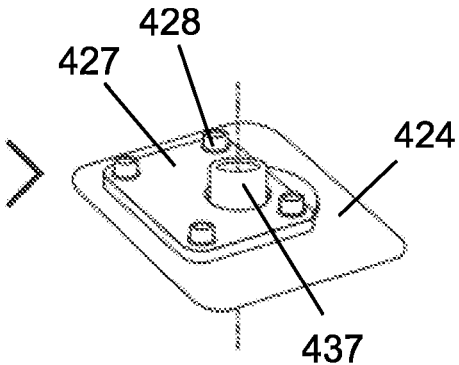
Fig. 28B	Fig. 28C
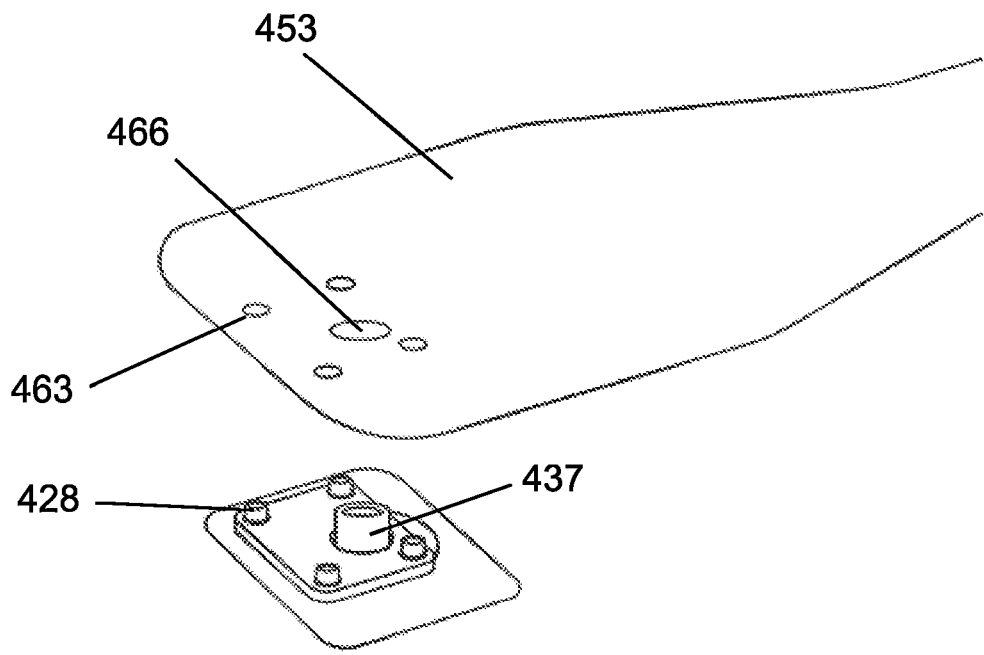
Fig. 28D

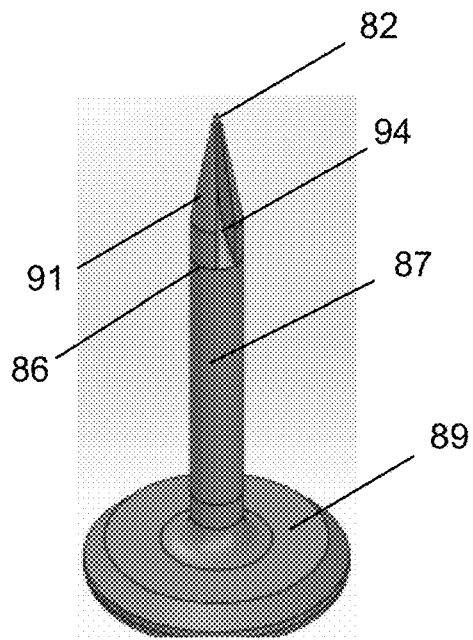
Fig. 36
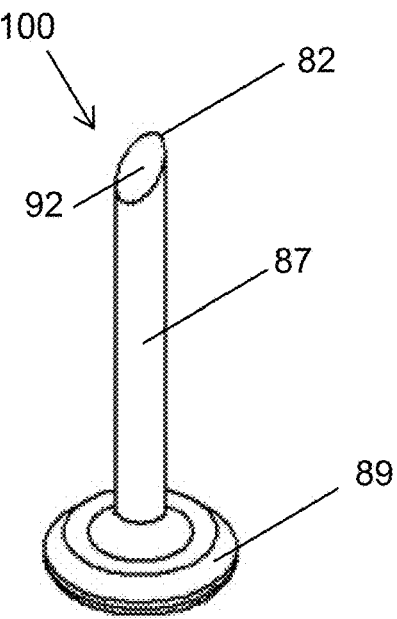
Fig. 37
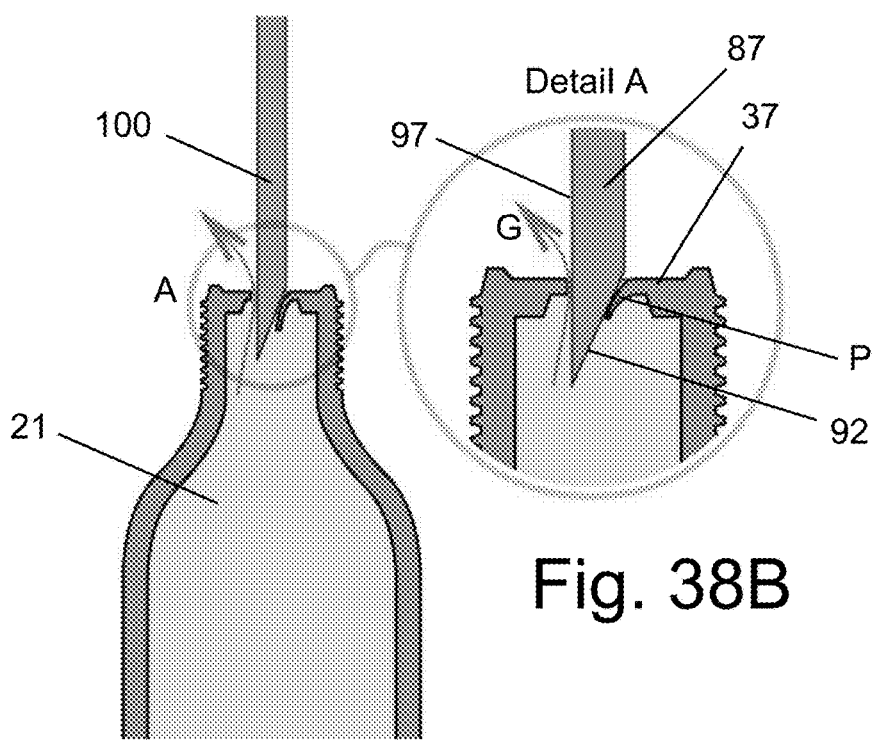
Fig. 38A
Fig. 38B ns having
TOURNIQUET

CROSS-REFERENCE TO RELATED APPLICATIONS

This application is a Continuation-in-Part application of International Patent Application PCT/IL2019/051154 filed on Oct. 24, 2019, which claims priority from Israeli Patent Application No. 262623 filed on Oct. 25, 2018.

FIELD OF THE INVENTION

The present invention relates to the field of inflatable tourniquets. In some embodiments, the invention relates to a pneumatically inflatable tourniquet for hemorrhage control that is adapted for use by both a paramedic and an unexperienced responder located unexpectedly at an emergency pre-hospital setting.

BACKGROUND OF THE INVENTION

A tourniquet is a well-known device for suppressing hemorrhaging. A strap, e.g. a bandage, twisted tight by an improvised implement such as a stick is traditionally used to apply pressure onto an artery and to therefore stop the flow of blood through a limb.

Other manually applied tourniquets using a force applier such as a ratchet or a windlass are able to stop the loss of blood from an injured arm within 20-80 seconds. However, a significantly larger force on the order of 300-600 N needs to be applied for a significantly longer duration, in order to suppress the hemorrhaging of the femoral artery, due to the increased depth thereof with respect to the skin surface relative to that of the brachia I artery, and due to the greater dimensions of the thigh relative to the arm. The actual force needed to suppress hemorrhaging is dependent upon the thickness of the limb, the depth of the artery within the limb and the width of the strap transmitting the applied force to the wounded artery. The width of the strap is generally limited in order to reduce the magnitude of the manually applied force needed to suppress hemorrhaging. Damage to soft tissue, muscles, nerves and bones within the wounded limb is liable to result, particularly due to the narrow dimension of the strap of approximately 2.5 cm that cuts into the skin, if an excessive force is applied.

It would be desirable to provide a pneumatically applied tourniquet having a relatively wide strap that is able to apply a uniform pressure onto a wounded limb despite the sufficiently high hemorrhage suppressing force being applied thereby and that is therefore unpainful to soft tissue.

Pneumatic tourniquets are commonly used in extremity surgery to achieve a nearly bloodless surgery while being able to apply a relatively high hemorrhage suppressing force onto a wounded limb. Such prior art pneumatic tourniquets comprise an inflatable cuff, which is a type of strap configured with a rubber bladder positioned within a plastic or fabric covering. Connective tubing is used to connect the cuff to a pressure device that includes an air compressor, buttons for setting the pressure, a digital display of the pressure setting, and a timer. The pressure device is powered by electricity, and is therefore connected to a wall outlet. The apparatus associated with these prior art pneumatic tourniquets is accordingly stationary, and is not useful to medics that need to treat wound victims at remote locations. Also, the wide straps used in a hospital setting, which may have a width on the order of 20 cm, are bulky, and are not readily transportable in a compact pouch so as to be useful to medics.

Disadvantages of other prior art pneumatic tourniquets include the lack of protection of the source of pressurized gas needed to inflate a strap, and therefore the unsuitability for use in a battlefield environment, and the inability to use the source of pressurized gas for more than one hemorrhage suppression operation.

Wounded victims are prone to ischemia within limb tissues during prolonged use of a tourniquet, as a result of the stop of blood flow distal to the tourniquet. The level of the ischemic changes is dependent on the duration during which the limb has been obstructed. These symptoms may be reversible if the pressure applied by the tourniquet is for a short term of less than two hours, or is periodically released for short intervals of a few minutes while allowing some bleeding to recur. However, medics are discouraged in releasing the pressure before the victim is brought to a hospital, such as by deflating the pressure within the strap if a pneumatic tourniquet is employed, due the occurrence of incremental exsanguination which can lead to death. After deflation of a pneumatic tourniquet, products of acidosis, lactate, toxic metabolites and oxygen free radicals are introduced into the blood system and cause complications such as systemic metabolic changes and reperfusion syndrome that might lead to cardiac arrest.

Moreover, if a pneumatic tourniquet were temporarily deflated in a pre-hospital setting, the stored pressurized gas would become depleted while the strap interior is exposed to atmospheric air, and therefore the pneumatic tourniquet could not be used after being deflated.

It is an object of the present invention to provide a pneumatic tourniquet for use by both a medic and an unexperienced responder in an emergency pre-hospital setting, in order to inflate a strap applying a hemorrhage suppressing force to a predetermined pressure.

It is an additional object of the present invention to provide a pneumatic tourniquet that is not injurious to both adult and pediatric wounded victims while the inflated strap is being applied.

It is an additional object of the present invention to provide a compact, reliable and user friendly pneumatic tourniquet that can be readily deployed at remote locations.

It is yet an additional object of the present invention to provide a pneumatic tourniquet that is adapted for use by a physician to temporarily deflate the strap, if need be.

It is yet an additional object of the present invention to provide a pneumatic tourniquet having a flow control unit that can be used for a plurality of hemorrhage suppression operations.

It is yet an additional object of the present invention to provide a pneumatic tourniquet that reduces the consumption of pressurized gas used for each hemorrhage suppression operation.

Other objects and advantages of the invention will become apparent as the description proceeds.

SUMMARY OF THE INVENTION

A tourniquet for use by different sized wound victims comprises a strap wrappable around a wounded limb to provide a desired hemorrhage suppressing force which is configured with first and second sections of different widths, wherein said second section is a pressure applying section which is significantly thinner and longer than said first section and said first section is adapted to transmit a hemorrhage suppressing force to the wounded limb of a significantly smaller magnitude than that of said second section.

A pneumatic tourniquet comprises an inflatable strap adapted to receive pressurized gas and to be wrapped around a wounded limb to provide a desired hemorrhage suppressing force.

In one embodiment, the pneumatic tourniquet further comprises a constricting device adapted to receive a free end of said strap in such a way that said free end is unrestrainably displaceable within said constricting device until being clamped thereby when said strap is sufficiently tensioned to transmit the hemorrhage suppressing force. The constricting device may comprise a housing member and a rocker rotatably mounted onto, and within, said housing member by a longitudinally extending axle, said rocker being configured to be angularly displaced about said axle until a surface of said rocker is set in clamping relation with a clamping edge of said housing member while said strap is interposed between said rocker surface and said clamping edge, in response to a force applied by the wounded limb onto said rocker when said strap is sufficiently tensioned.

In one aspect, the pneumatic tourniquet further comprises a sealing element, wherein a clamping force applied by said rocker surface and said clamping edge onto said sealing element prevents flow of the pressurized gas from a pressure applying section of said strap which is wrapped around the wounded limb to said free end, allowing said strap free end to be considerably thinner than said pressure applying section.

In one aspect, the sealing element is provided internally within the strap, the strap being configured with an inner layer, an outer layer, and an intermediate sealant layer that are interconnected.

In one aspect, the sealing element is external to the strap.

A user-friendly gas flow control assembly of a pneumatic tourniquet comprises a casing which contains a housing with which a gas cartridge filled with pressurized gas and normally sealed by an occluding element is coupleable, a longitudinally displaceable force transmitting element, and an outlet port; a pivotable activation handle configured with a wide-area, substantially planar user-manipulatable surface; and a structure provided with said casing which cooperates with said activation handle to define an axis of rotation of said activation handle, wherein, upon pivoted displacement of said activation handle about its axis of rotation, an activation force is transmitted that drivingly contacts said force transmitting element to forcefully contact and open at least a portion of said occluding element, causing the pressurized gas to be discharged from said gas cartridge and flow via said outlet port to an interior of an inflatable strap which is wrappable around a wounded limb to provide a desired hemorrhage suppressing force.

In one aspect, the occluding element is a puncturable cover and the force transmitting element is a puncture pin that terminates with a pointed end that is drivable to an inwardly displaced position at which the pointed end punctures the puncturable cover.

In one aspect, the puncture pin has, for at least one region thereof, a solid shaft of a uniform diameter that is cut at an angle to define a planar surface having a sharp peripheral edge configured such that the pointed end is coincident with the peripheral edge and with an outer surface of the shaft, producing an unsealed passageway adjoining the shaft outer surface along which the pressurized gas is discharged from the gas cartridge following puncturing of the cover by the pointed end.

In one aspect, the force transmitting element is an activation piston configured to cooperate with a valve stem associated with the gas cartridge.

In one aspect, the structure provided with said casing which cooperates with said activation handle to define the axis of rotation is a laterally extending beam which is rotatably mounted in corresponding seats provided with said casing to define the axis of rotation of said activation handle. A cam which is fixedly connected to said beam may be in drivable proximity with said force transmitting element.

A flow control unit (such as a pressure regulating unit) which comprises a housing member configured with an inlet for receiving pressurized gas upon demand and with an internal cavity; a hollow tube having an outer diameter of less than 2.5 mm which is in fluid communication with said inlet; an intermediately bored piston connected to, and which has an outer diameter significantly greater than, said tube, said piston being axially and sealingly displaceable within said internal cavity to define at a distal end thereof a supply chamber in fluid communication with atmospheric air and, at a proximal end thereof, a regulating chamber which is in fluid communication with said inlet via said tube; and a fixed sealing element, wherein, following flow of the pressurized gas into said regulating chamber, said piston is caused to be distally displaced by a pressure differential between the pressure in said regulating chamber and in said supply chamber until a distal end of said tube is occluded by said sealing element, to prevent additional inflow of the pressurized gas.

A pneumatic tourniquet comprises an inflatable strap wrappable around a wounded limb to provide a desired hemorrhage suppressing force; and a pressure regulating unit configured with an inlet for receiving pressurized gas upon demand; a piston axially and sealingly displaceable within an internal cavity to define at a distal end thereof a supply chamber in fluid communication with atmospheric air and, at a proximal end thereof, a regulating chamber which is in fluid communication with said inlet and with an interior of said strap; and a manual pressure release initiator, which, when displaced, provides a clearance that is in fluid communication with said regulating chamber and with atmospheric air to selectively reduce the pressure of the fluid within said strap interior while preventing additional inflow of the pressurized gas to said regulating chamber.

A puncture mitigating connection section for connecting an inflatable strap to a gas flow control assembly casing comprises a flexible inlet port protruding through an external layer of an inflatable strap and having a central passageway which is in fluid communication with an interior of the strap, wherein said inlet port is coupleable with a discharge port of a gas flow control assembly through which pressurized gas for inflating the strap is dischargeable; and a plurality of fastening means protruding from the external layer of the strap and separated from said inlet port, wherein each of said fastening means is coupleable with a corresponding fixed element associated with a casing of the gas flow control assembly.

In one aspect, the plurality of fastening means are integrally formed with a rigid plate positioned within the strap interior and attached to the external strap layer and formed with an aperture through which the inlet port protrudes.

In one aspect, the rigid plate is attached to a semi-rigid sealing layer adapted to provide added protection against efflux of the pressurized gas from the connection section and a mounting element of the inlet port is attached to said semi-rigid sealing layer.

As referred to herein, "longitudinally" means along a direction parallel to the axis of a tubular gas cartridge, when coupled with the puncture unit housing. "Lateral" means in a direction substantially perpendicular to the longitudinal direction. "Transversal" means in a direction at an angle to the longitudinal direction which is not necessarily the lateral direction. "Proximal" means in a direction towards a user accessible element of the tourniquet, such as the manual pressure release initiator or an unattached edge of the activation handle distant from its axis of rotation. "Distal" means in a direction opposite to the proximal direction. Other directional terms, such as "top", "above" and "below" refer to an orientation when the tourniquet is disposed on top of a horizontal surface, although the tourniquet may be disposed at any other desired orientation.

BRIEF DESCRIPTION OF THE DRAWINGS

In the drawings:

FIG. 10 is a plan view of components associated with the gas flow control assembly, shown when removed from the casing;

FIG. 11 is a cross sectional view of the components of FIG. 10, cut along a horizontal plane;

FIG. 27A is a top view of the entire strap of FIG. 26, shown in a flattened condition;

FIG. 27B is a side view of the strap of FIG. 27A, when inflated;

FIG. 28B is an exploded perspective view of components used to produce the connection section of FIG. 28A;

FIG. 28C is a perspective view of the components of FIG. 28B, when attached together;

FIG. 28D is an exploded perspective view of the attached components of FIG. 28C when positioned in underlying relation to an external surface of an inflatable strap, prior to attachment thereto;

FIG. 36 is a perspective view from the front of an embodiment of a puncture pin;

FIG. 37 is a perspective view from the front of another embodiment of a puncture pin;

FIG. 38A is a schematic illustration of a gas cartridge cover being punctured by the puncture pin of FIG. 37; and FIG. 38B is an enlargement of Detail A of FIG. 38A.

DETAILED DESCRIPTION OF THE INVENTION

The compact pneumatic tourniquet of the present invention is used primarily, but not necessarily, in emergency settings, such as following a motor vehicle crash, an explosion, a stabbing incident or on the battlefield in an attempt to stop extremity bleeding and death due to blood loss. Pressure is applied circumferentially around a portion of the wounded limb, after the strap is inflated to a predetermined pressure, causing the blood vessels to which the pressure is applied to become temporarily occluded.

By virtue of its user-friendly configuration, the tourniquet is easily activated by all users, including paramedics, unexperienced responders located unexpectedly at an emergency setting and even the wounded victim, to initiate a hemorrhage suppression operation and the strap is easily wrapped around the wounded limb and tensioned.

The unique configuration of the tourniquet, as will be described hereinafter, dramatically reduces the complications normally associated with the prolonged use of a tourniquet, and injury to skin and subcutaneous tissues as a result of excessive pressure applied to pediatric victims.

Since the pressurized gas for use by the pneumatic tourniquet is supplied internally within the casing of a gas flow control assembly, generally by means of a gas cartridge, and not externally to the casing by electrically operated gas transfer equipment as practiced by the prior art, the compact tourniquet of the present invention lacks any electrical or electronic components, and can advantageously be used in wet or muddy environments. Of course in some embodiments, a well-sealed electronic module, such as one comprising a GPS component for locating a subject or sensors for determining some of the subject's real-time physiological characteristics, similar to an electronic module provided to a diver, may be added.

Figure 1:
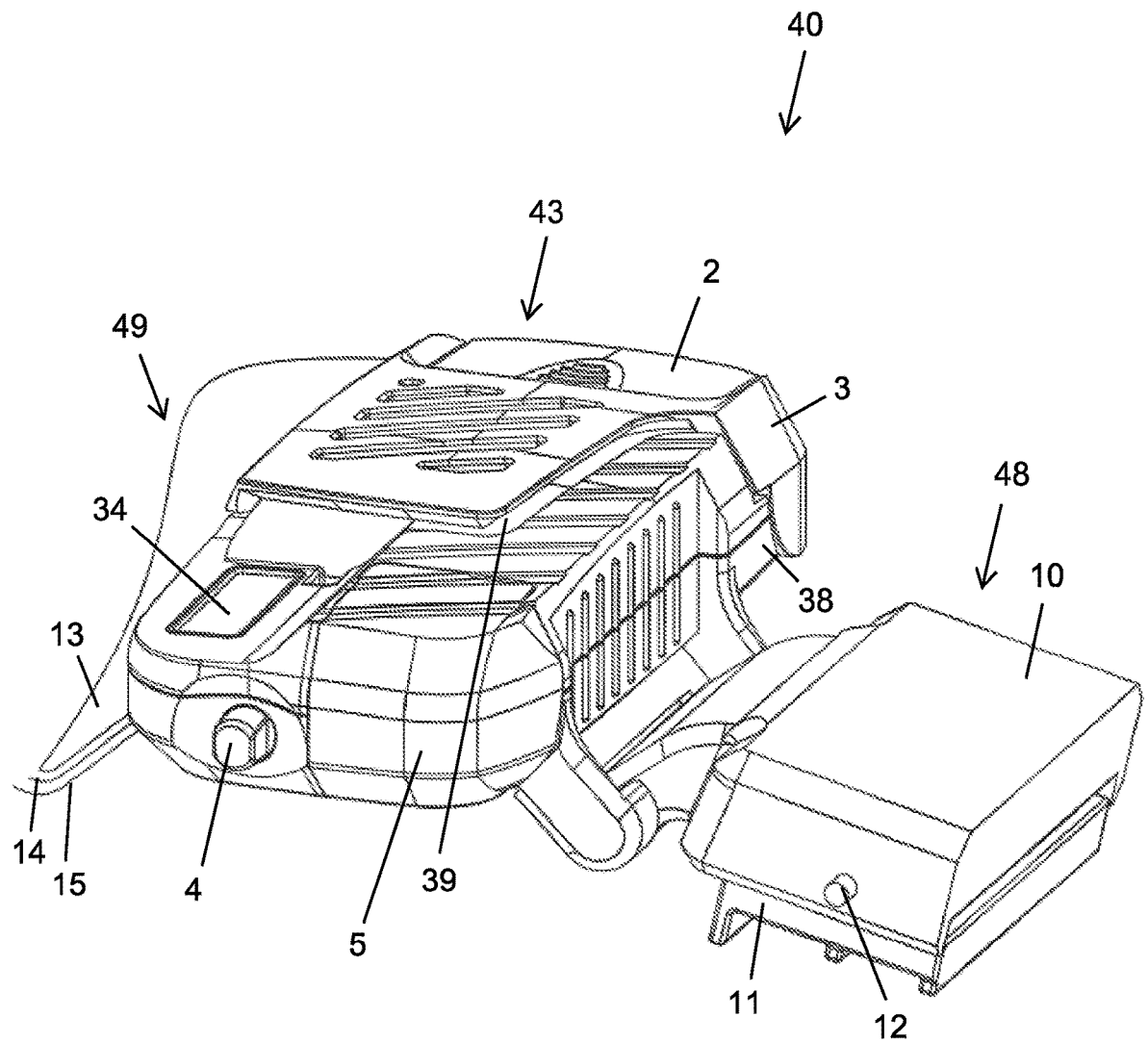
FIG. 1 is a perspective view from the top of an embodiment of a pneumatic tourniquet, shown when the constricting device is in an opened position and the inflatable strap is only partially illustrated.
Figure 2:
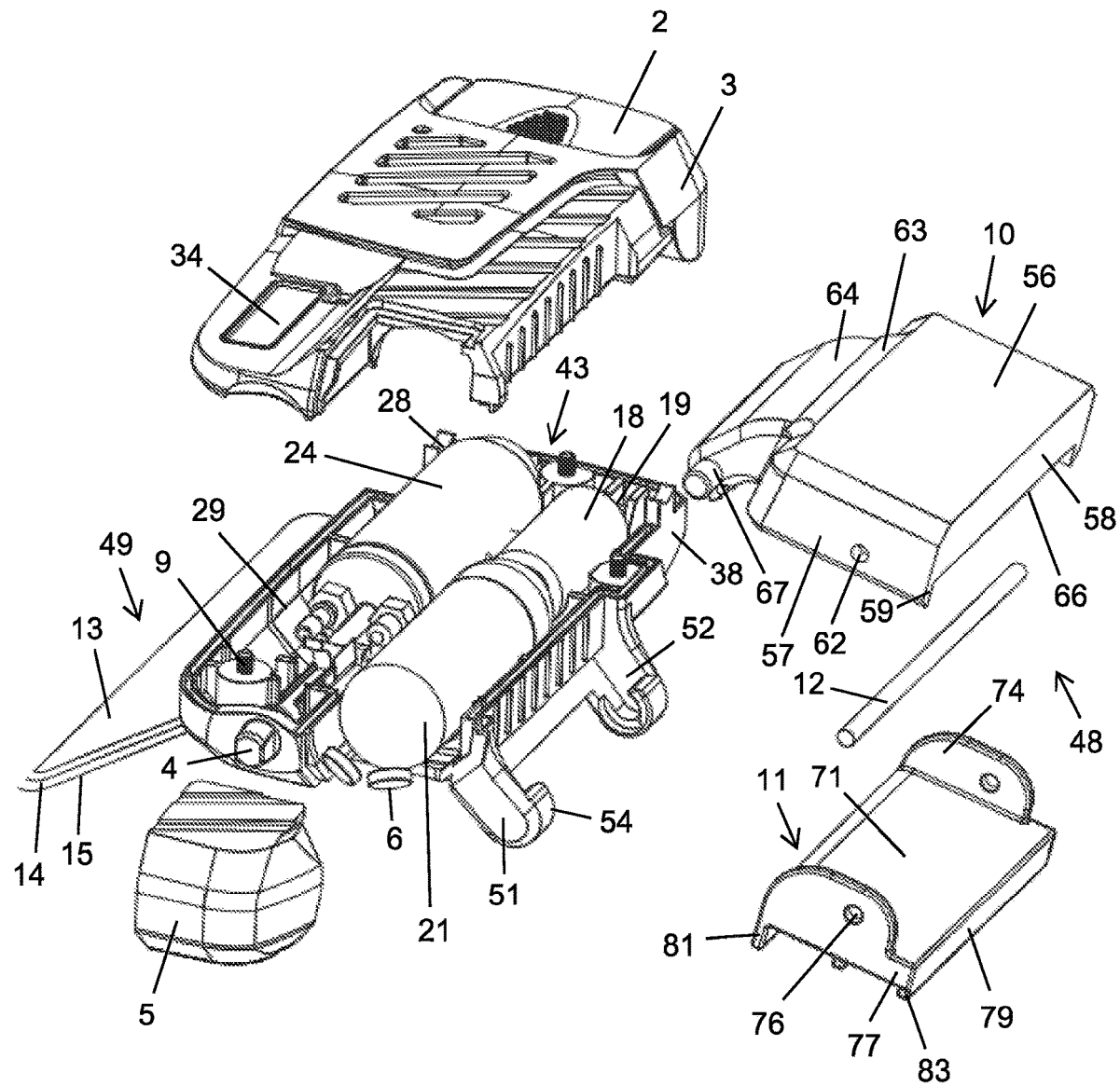
FIG. 2 is an exploded view of the tourniquet of FIG. 1.

FIGS. 1 and 2 illustrate an embodiment of pneumatic tourniquet 40. Pneumatic tourniquet 40 comprises gas flow control assembly 43, constricting device 48 pivotally connected to gas flow control assembly 43, and inflatable strap 49 which is connected to gas flow control assembly 43 and is selectively clamped by constricting device 48.

Inflatable strap 49 may be configured with three layers 13-15 of substantially equal lengths and widths. Inner layer 15 is made of a flexible tear resistant material. Outer layer 13, which is exposed to the underlying terrain often having sharp objects such as thorns and broken glass, is made of a flexible and puncture resistant material such as silicone elastomer or a fabric made of a flexible material, e.g. nylon or polyester, and sealed with a puncture resistant material layer, e.g. polyurethane. The intermediate layer 14 is made of a sealant such as polyurethane.

Gas flow control assembly 43 is configured with a casing, e.g. a casing having an upper section 2 and a lower section 38 according to the illustrated orientation to form a curved proximal user-accessible surface. Upper casing section 2 and lower casing section 38 may be coupled together by a plurality of spaced fasteners 9, e.g. threaded fasteners. Two longitudinally spaced arms 51 and 52 may extend downwardly from the same side of lower casing section 38, and each terminates with a corresponding arcuate protruding seat 54. The two seats 54 face each other.

Within gas flow control assembly 43 are mounted a replaceable gas cartridge 21, puncture unit housing 18 within which a metallic cover normally sealing gas cartridge 21 is punctured in order to enable pressurized gas, e.g. carbon dioxide or nitrogen, to be discharged from the gas cartridge, a pressure regulating unit 24 for controlling the pressure of gas discharged into the interior of inflatable strap 49, and manual pressure release initiator 4 operatively connected to pressure regulating unit 24 for selectively deflating strap 49 while ensuring that the remaining pressurized gas within gas cartridge 21 will not be discharged. Manual pressure release initiator 4 may protrude from the curved proximal surface of the casing.

Gas cartridge 21 may be supplied with carbon dioxide, nitrogen, a noble gas or a refrigerant gas. The gas, which is compressed at a pressure of 70-170 bar at 60° C. and approximately 20 bar at −10° C., is replaceable upon removing cartridge cover 5. Cover 5 may have, for example, a width of approximately one-half the casing width, a length of approximately a fourth of the casing length, and a height approximately equal to the total thickness of upper casing section 2 and lower casing section 38, or any suitable dimensions. Cartridge cover 5 may be releasably secured to the casing by means of one or more magnets 6, which are attached to lower casing section 38.

Alternatively, gas flow control assembly 43 may be configured without a pressure regulating unit or without a puncture unit housing. When the gas flow control assembly is configured without a puncture unit housing, another type of force transmitting element, such as element 472 shown in FIG. 30, may be selectively driven to forcefully contact and open at least a portion of an occluding element normally sealing gas cartridge 21, to facilitate flow of the pressurized gas from the gas cartridge and into to the interior of inflatable strap 49.

Alternatively, the gas flow control assembly is provided with an irreplaceable gas cartridge and is accordingly configured without a cartridge cover.

A thin and wide-area activation handle 3 for initiating inflation of strap 49 is pivotally connected to a distal region of the casing of gas flow control assembly 43. Activation handle 3 is rendered to be of a user-friendly wide area when its width is more than 60% of the width of gas flow control assembly 43. Activation handle 3 normally overlies a recess 39 formed in upper casing section 2 by a small interspace sufficient to insert a portion of a finger therein, e.g. 0.5 cm, and to pivotally raise handle 3. The thickness of activation handle 3 is generally uniform; however, it may increase gradually, for example from 1 mm in the region contacted by the fingers to maximize the finger clearance to 3 mm in the region of the pivot axis, so as to increase the overall structural strength of the activation handle. Activation handle 3 is substantially planar to reduce the amount of material needed, although it may be somewhat curved, while of substantially high structural strength in order to be able to transmit an activation force, as will be described hereinafter.

In one embodiment, recess 39 extends distally to timer device 34, e.g. a digital timer device, adapted to indicate the initiation of a hemorrhage suppression operation, which is housed in the half of upper casing section 2 not occupied by cartridge cover 5 being distally to the curved proximal surface.

Constricting device 48 for clamping inflatable strap 49 when sufficiently tensioned comprises housing member 10 and rocker 11 rotatably mounted onto, and within, housing member 10 by axle 12.

Housing member 10 has a thickened terminal wall 56, which may be planar and rectangular, and an outer wall 58 and two longitudinally spaced side walls 57 that extend downwardly from upper wall 56 to a height below the lower surface of terminal wall 56 to define a protruding portion 59, with respect to the illustrated orientation. The lower edge 66 of outer wall 58 constitutes a clamping edge. An aperture 62 is bored in each side wall 57, so that the two apertures 62 are aligned. A curved element 64 extends downwardly from the inner edge 63 of upper wall 56, and terminates with two hinge elements 67 longitudinally extending in opposite directions that are received in corresponding seats 54, allowing housing member 10 to rotate about the axis coinciding with seats 54.

Rocker 11 has a planar surface 71, which may be rectangular, and two longitudinally spaced side walls 74 that upwardly extend from surface 71 and that may be upwardly curved. Each side wall 74 may have a short portion 77 that laterally projects from the curved portion and whose upper edge is coplanar with surface 71. Short inner 81 and outer 83 legs extending longitudinally between the two side walls 74 may extend downwardly from surface 71. The longitudinal spacing between side walls 74 is less than that of side walls 57 of housing member 10. An aperture 76 is bored in each side wall 74, preferably in a region closer to the corresponding short portion 77, such that the two apertures 76 are aligned. Axle 12 is adapted to be received within apertures 62 and 76, to allow rocker 11 to swing thereabout. An outer wall 79, i.e. facing away from arms 51 and 52, longitudinally extends between the two short portions 77 and upwardly extends from surface 71 to a height significantly less than that of side walls 74.

Figure 3:
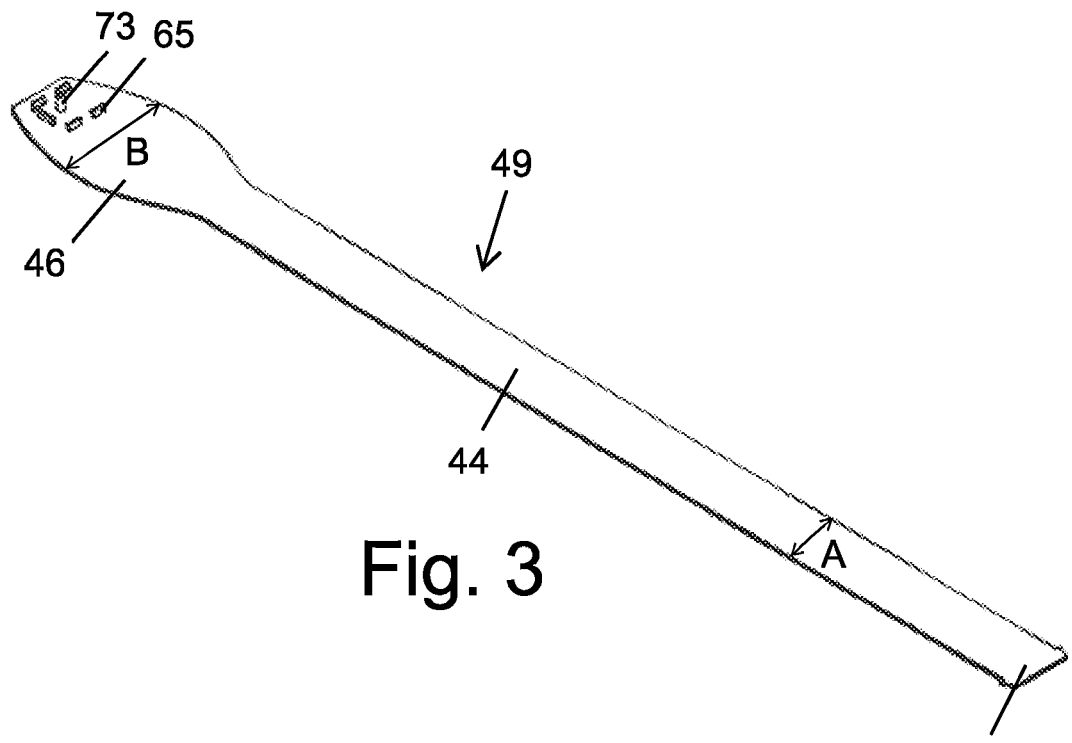
FIG. 3 is a perspective view from the top of an inflatable strap usable in conjunction with the tourniquet of FIG. 1, shown in a flattened condition.

FIG. 3 illustrates a top view of inflatable strap 49 when flattened out. Strap 49 may be configured with two integral sections 44 and 46 of different widths. Section 44 of uniform width A, e.g. 50 mm, is elongated, and is adapted to be wrapped around a wounded limb in order to apply circumferential pressure and to suppress hemorrhaging. Section 46 of maximum width B greater than width A, e.g. 100 mm, which is connectable to the casing of the gas flow control assembly for increased connection strength, may be configured with a curved, e.g. elliptical, periphery. By providing a strap with a relatively narrow pressure applying section, the constricting device through which strap 49 is freely displaceable until being restrained may advantageously be narrow as well, to achieve a compact device. The short terminal end 45 of strap 49 being opposite to connection section 46, which is included in the free end of the strap that is pulled during a tensioning operation, may have a width that is slightly greater than A, e.g. 60 mm, in order to prevent retraction of the free end in an opposite direction through the constricting device.

As opposed to manually applied tourniquets which are narrow, generally having a strap width of up to 5 cm due to the difficulty in applying the required hemorrhage suppressing force, the pneumatic tourniquet of the present invention is capable of achieving sufficiently high pressures for applying a hemorrhage suppressing force to even very large diameter limbs. A strap 49 configured with two integral sections 44 and 46 of different widths has significant clinical advantages in that a hemorrhage suppressing force will not be transmitted entirely by relatively narrow section 44. Wrapping a relatively wide strap section 46, e.g. of 15 cm, around the limb or at least most of the limb leads to even distribution of the pressure applied onto the surface of the limb and helps to diminish pain and local damage, advantages which are of much importance with respect to subjects having a small limb diameter, such as in pediatric patients. At the same time, a relatively high hemorrhage suppressing force may be transmitted via relatively long and narrow section 44 to adult victims having relatively large-diameter limbs without undue pain and damage to tissue.

In one embodiment, the two sections 44 and 46 are made of different materials that have a different degree of flexibility. The relative width of sections 44 and 46 accordingly may change after strap 49 is inflated. For example sections 44 and 46 may have the same width prior to the inflation of the strap; however following inflation, section 44 becomes thinner and longer than section 46.

It will be appreciated that an inflatable strap may have a uniform width.

In one embodiment, the strap provided with sections 44 and 46 of different widths may be uninflatable. Sections 44 and 46 may be integrally formed with the uninflatable strap, or alternatively may be connected together, e.g. releasably connected together, by various means well known to those skilled in the art such as adhesion, sewing, fusion, buttons, and hook-and-loop fasteners.

Figure 7:
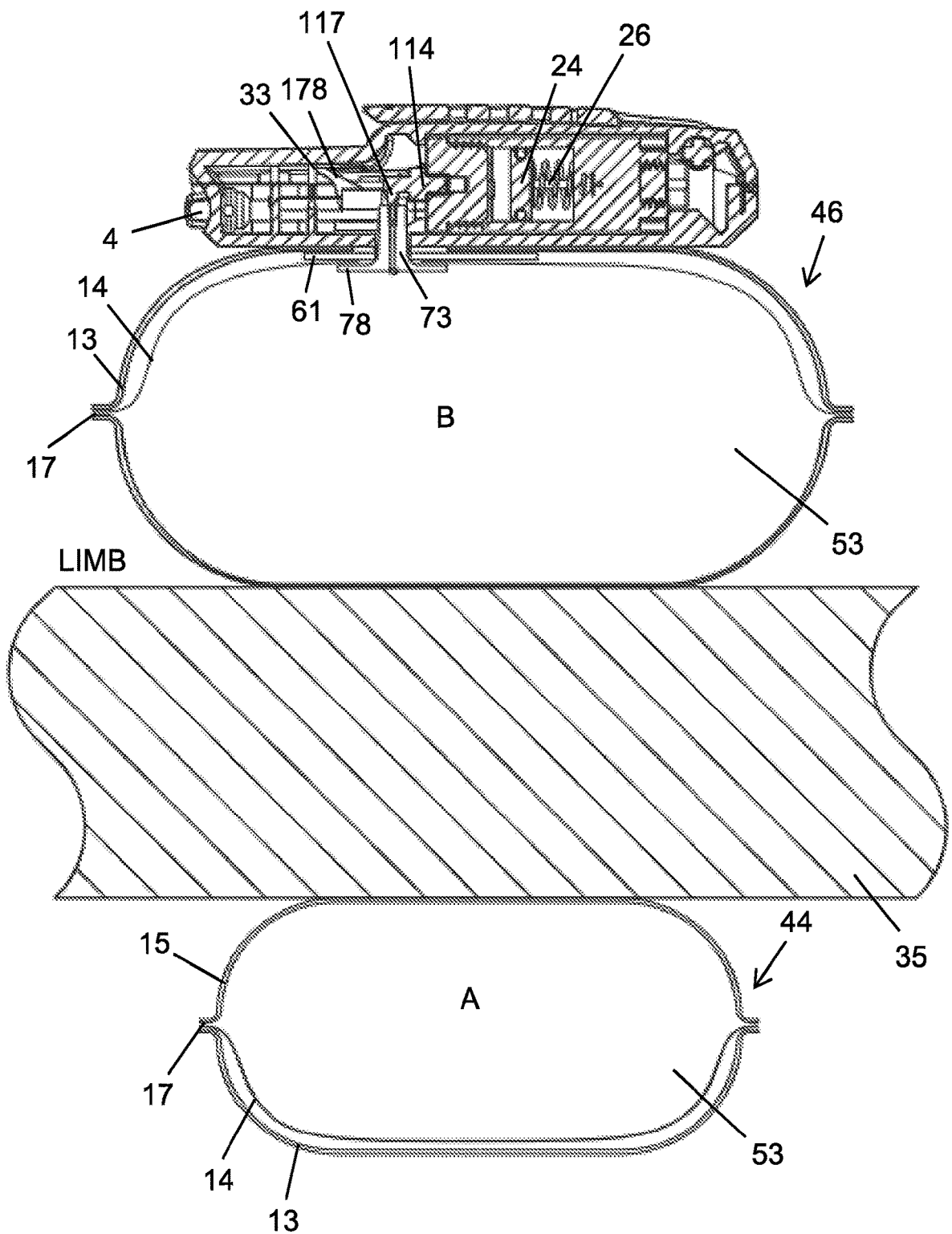
FIG. 7 is a cross sectional view of the tourniquet of FIG. 1 when deployed during a hemorrhage suppression operation, cut along a medial plane through the gas flow control assembly, two separated portions of the strap when inflated, and the wounded limb.

Connection section 46, as shown in FIG. 7, is internally provided with a relatively rigid attachment plate 61 adapted for attachment to the gas flow control assembly casing, in addition to outer layer 13, intermediate sealant layer 14 and inner layer 15 of the inflatable strap. Inner layer 15 is adapted to be in contact with a wounded limb 35. Internal attachment plate 61, which may be made of a relatively rigid plastic such as polypropylene or high-density polyethylene, is connected between outer layer 13 and sealant layer 14, such as by welding. The three layers 13-15 may be welded together by a welding line 17 that extends lengthwise along the entire corresponding widthwise edge of the inflatable strap that includes both pressure applying section 44 and connection section 46.

As further shown in FIG. 3, a plurality of separated snapping fasteners 65, or any other suitable type of fasteners such as screws or clips, connected to the attachment plate protrude outwardly within connection section 46 from the outer strap layer. Also protruding outwardly from the outer strap layer is a tubular port 73 for the passage therethrough of pressurized gas into the strap interior, which is positioned generally centrally with respect to the plurality of fasteners 65.

Figure 4:
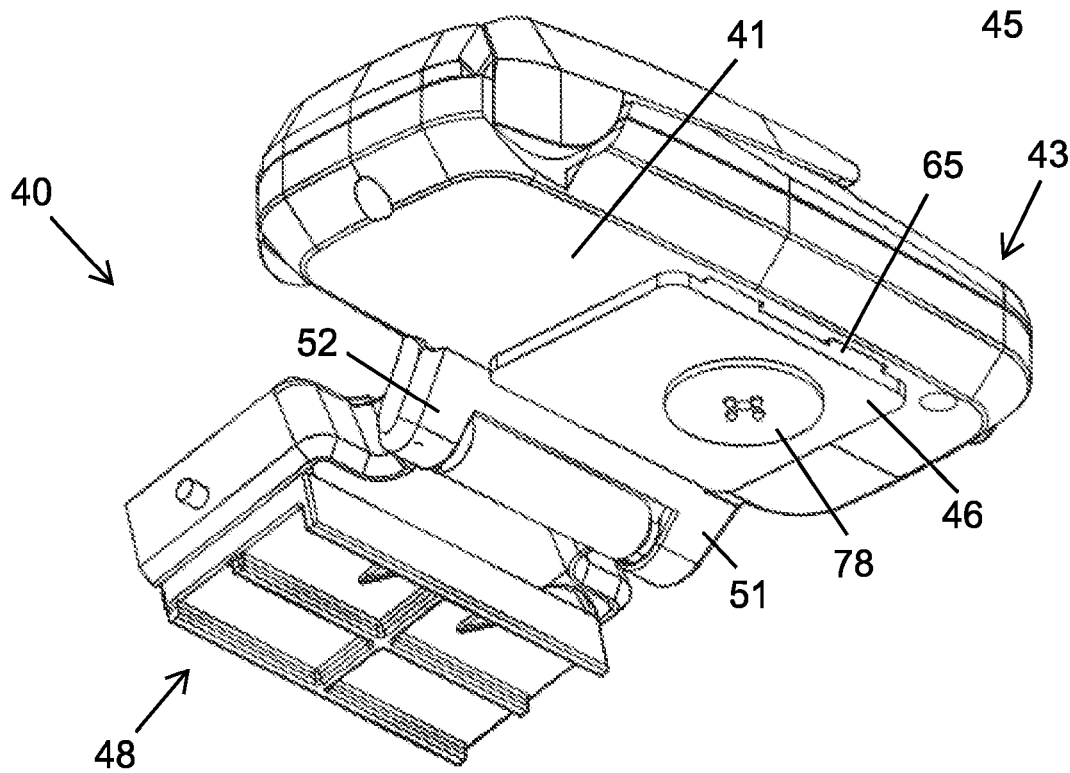
FIG. 4 is a perspective view from the bottom of the tourniquet of FIG. 1, shown when the constricting device is in an opened position and the inflatable strap is removed.
Figure 5:
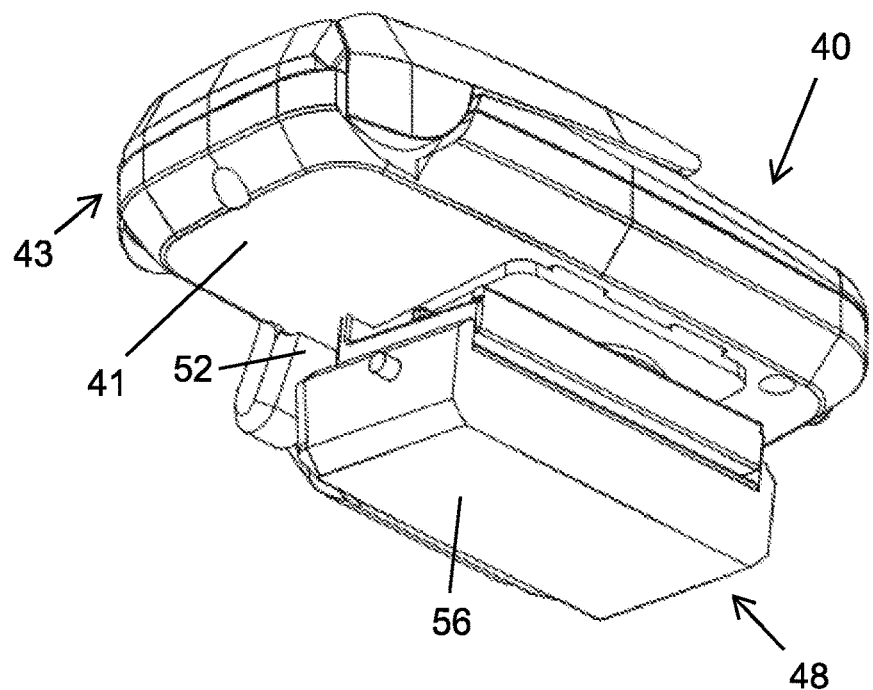
FIG. 5 is a perspective view from the bottom of the tourniquet of FIG. 1, shown when the constricting device is in a closed pivoted position and the inflatable strap is removed.

FIGS. 4 and 5 illustrate tourniquet 40 from below when constricting device 48 is set to an opened position suitable for cooperating in performance of a hemorrhage suppression operation and to a closed pivoted position, respectively, suitable to be compactly stored in a pouch in preparation to being dispatched during an emergency setting to assist a wounded victim. When constricting device 48 is set to the pivoted position, the hinge elements rotate approximate 180 degrees until terminal wall 56 of the housing member is substantially parallel to the underside surface 41 of the casing of gas flow control assembly 43.

When the strap is uninflatable, a small member from which downwardly extend arms 51 and 52 (FIG. 2) may be secured to the strap in lieu of the casing of the gas flow control assembly.

Strap 49 shown in FIG. 3 may also be compactly stored, for example after being wrapped about itself, in the same or a different pouch as the pivoted constricting device and gas flow control assembly.

Figure 6:
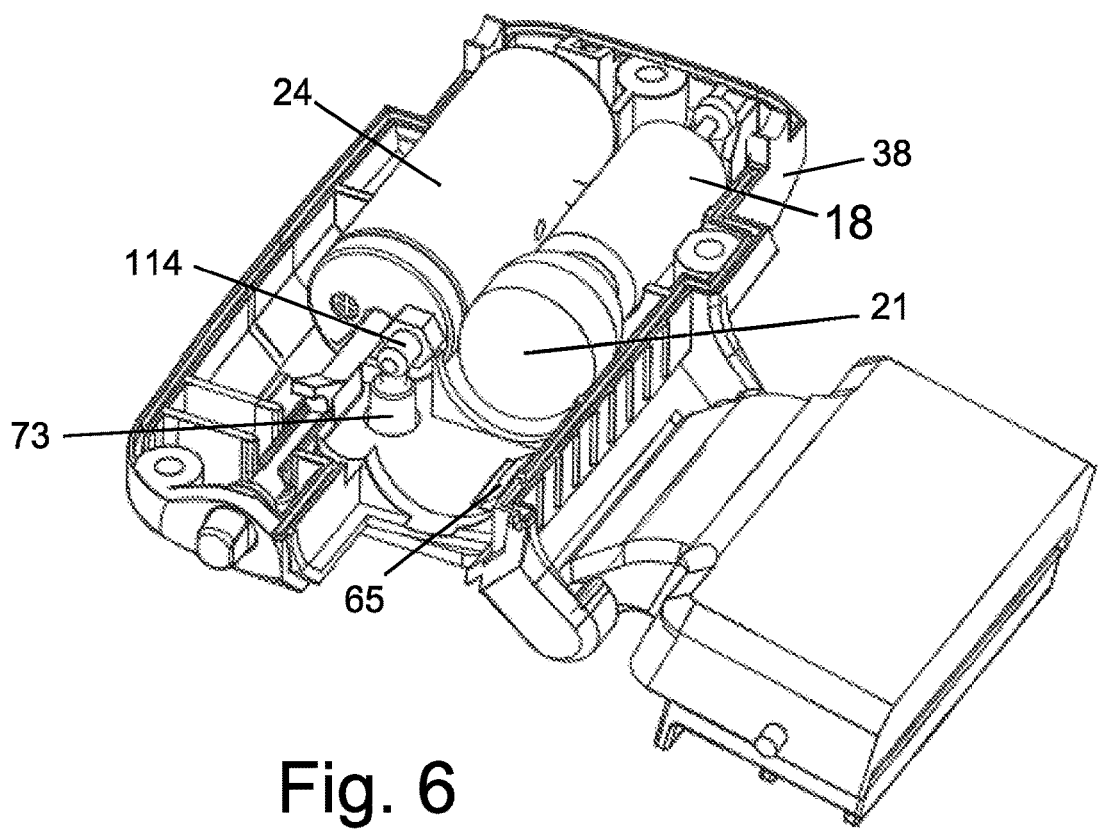
FIG. 6 is a perspective view from the top of the tourniquet of FIG. 1, shown when the upper casing of the gas flow control assembly is removed and the gas cartridge is partially removed to illustrate fasteners connecting the inflatable strap to the lower casing.

As shown in FIGS. 4 and 6, partially illustrated connection section 46 of the inflatable strap is positioned in abutting relation with casing underside surface 41 by the plurality of snapping fasteners 65, which are attached to a portion of lower casing section 38 located below the partially illustrated gas cartridge 21, when coupled to puncture unit housing 18.

Some elements that enable the flow of pressurized gas into the interior 53 of the inflated strap 49 are illustrated in FIGS. 4, 6, 7 and 17. The flow of pressurized gas discharged from the gas cartridge is directed to the interior 53 of the inflatable strap by means of centrally bored port 73. Port 73 may be part of an element that is coupleable, e.g. releasably coupleable, with gas flow control assembly 43 prior to performance of a hemorrhage suppression operation. Such an element may comprise an integral abutment member 78 having a diameter, or maximum width, significantly greater than that of port 73. Tubular port 73 may be factory-secured to attachment plate 61 via an aperture formed in attachment plate 61 and in outer layer 13 and intermediate layer 14 of the inflatable strap, such that abutment member 78 is brought in pressing relation with attachment plate 61.

Port 73 may be coupled to pressure regulating unit 24 via a conical nipple 117 extending downwardly from a discharge conduit 114 of the pressure regulating unit by a simple pressing motion transmitted through coupling section 46. When coupling section 46 is attached to the casing underside surface, pressurized gas discharged from the gas cartridge will be directed via tube 26 of pressure regulating unit 24, discharge conduit 114, nipple 117 and port 73 to the interior 53 of the inflatable strap.

While pressurized gas is introduced to the common interior 53 of pressure applying section 44 and coupling section 46, inner layer 15 becomes separated from intermediate sealing layer 14 as the pressurize within interior 53 rises.

Alternatively, connection section 452 shown in FIGS. 28A-D may be employed.

Figure 8:
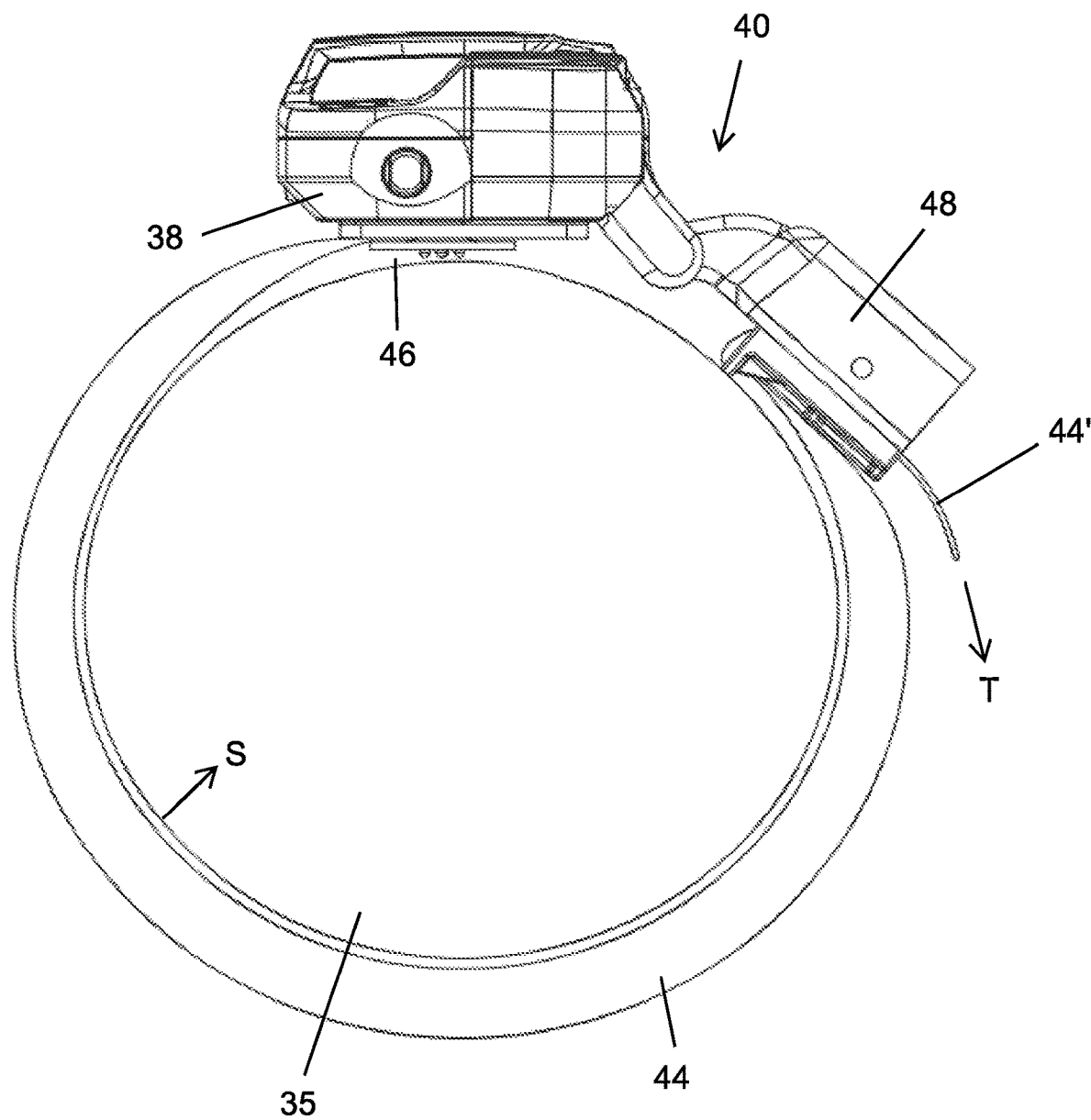
FIG. 8 is a cross sectional view of a wounded limb cut along a frontal plane, showing the tourniquet of FIG. 1 when deployed during a hemorrhage suppression operation such that the inflated strap is wrapped about the limb and set in a clamped relation with respect to the constricting device.

FIG. 8 illustrates pneumatic tourniquet 40 when deployed during a hemorrhage suppression operation. To ensure a speedy hemorrhage suppression operation, free end 44' of the strap is pre-fed through constricting device 48 while the tourniquet is stored. During an emergency setting, tourniquet 40 is first removed from its pouch and constricting device 48 is positioned at a selected region of wounded limb 35 relative to the wound site. Pressure applying section 44 is then wrapped around limb 35 until connection section 46 is attached to gas flow control assembly casing 38 while the latter remains in abutment with limb 35. Upon freely pulling on free end 44' of the strap by applying a force T in a direction away from constricting device 48, pressure applying section 44 becomes sufficiently tensioned to enable performance of the subsequent hemorrhage suppression operation after the discharge of pressurized gas from the gas cartridge has been initiated.

Figure 9:
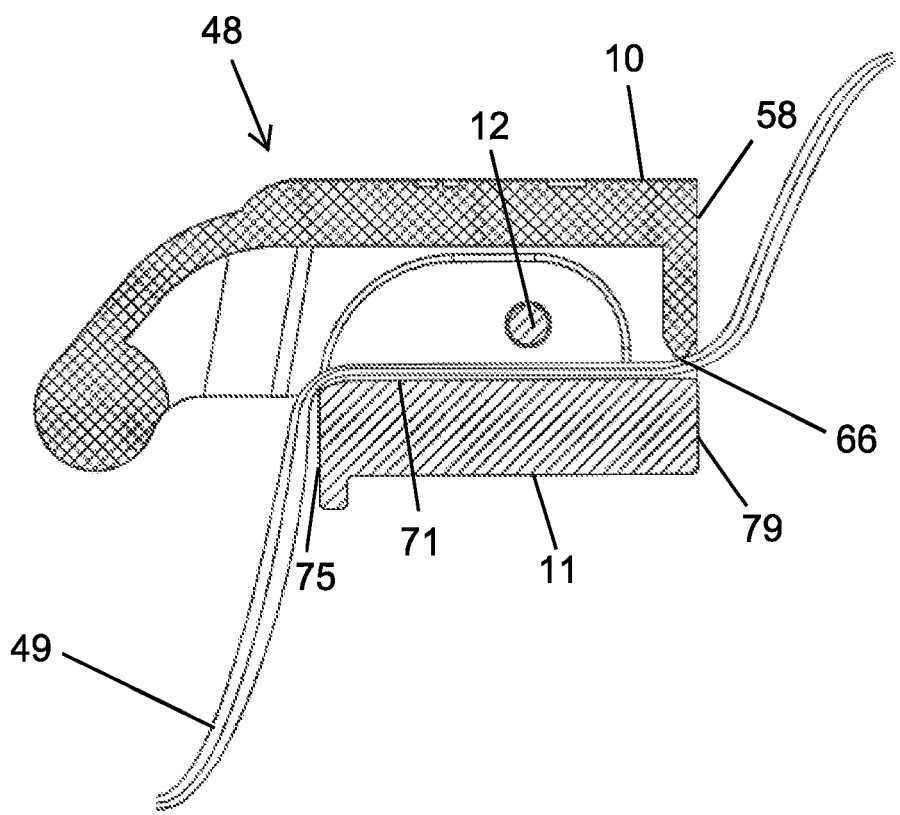
FIG. 9 is a cross sectional view of a constricting device used in conjunction with the tourniquet of FIG. 1, showing an inflatable strap being fed therethrough.

As shown in FIG. 9, strap 49 is positioned in movable contact with upper strap-engageable surface 71 of rocker 11 and below axle 12 while being fed through constricting device 48, for example at a factory or by a medical practitioner when the tourniquet is being deployed. When strap 49 is sufficiently tensioned while wrapped around the wounded limb, the limb applies a force to inner wall 75 of each side wall of rocker 11. This applied force causes rocker 11 to rotate about axle 12, in a counterclockwise direction according to the illustrated orientation, until the outer rocker wall 79 is brought in clamping relation with the clamping edge 66 of the outer wall 58 of housing member 10 while strap 49 is interposed between outer rocker wall 79 and housing member outer wall 58. The angular displacement of rocker 11 may also be facilitated by spacing axle 12 away from the vertical centerline of each side wall 74, to provide eccentric motion. At this clamping relation, the free end of strap 49 can no longer be freely pulled, but rather is clamped.

Manual pressure release initiator 4, whose operation will be described hereinafter, may be used to disengage the strap from clamping edge 66 by reducing the pressure within the strap interior and allowing the strap to be once again freely displaceable, or to release the pressure gradually before removing the tourniquet.

Referring back to FIG. 8, the clamping relation established between the outer rocker wall and the outer housing member wall advantageously also allows the strap free end 44' to be considerably thinner than pressure applying section 44 of the strap. When pressurized gas at a predetermined pressure is introduced into the interior of the strap, the strap becomes inflated and a radial hemorrhage suppressing force S is applied to limb 35. Without cooperation with constricting device 48, an inflated free end 44', which may have a length on the order of 30 cm, is liable to be bothersome, and times even injurious, to the wounded victim and to the health practitioner attempting to assist the victim. The outer rocker wall and the outer housing member wall, when a clamping relation is established at the clamping edge, both apply a clamping force to the intermediate sealant layer of the strap, thus preventing passage of the pressurized gas from pressure applying section 44 beyond the clamping edge to free end 44'. The intermediate sealant layer which is located close to the outer layer also assists in preventing seepage of the pressurized gas outwardly from the strap interior to the atmosphere.

Reference is now made to FIGS. 10-16, which illustrate the apparatus adapted to cooperate with puncture unit housing 18 in order to initiate discharge of pressurized gas from gas cartridge 21. The discharged gas flows via interconnecting structure 8 from puncture unit housing 18 to pressure regulating unit 24.

As shown in FIGS. 10 and 11, a puncture pin 19 normally protruding outwardly from puncture unit housing 18 when in a retracted position is subsequently axially displaceable within bore 88 formed within puncture unit housing 18.

Puncture pin 19, from example made of steel, is configured with a solid and uncompromised elongated shaft 87 that terminates with pointed end 82 which is adapted to puncture the metallic cover 37 of gas cartridge 21, after the latter has been inserted to a substantially fullest extent within puncture unit housing 18 via an opening at an end thereof opposite to puncture pin 19 by means of threaded engagement 36. Puncture pin 19 also has a large sized head element 89, which is contacted when a driving force is applied thereto by the activation handle and is caused to be displaced to an inwardly displaced position. Displacement of puncture pin 19 at a sufficiently high force to the inwardly displaced position causes pointed end 82 to puncture metallic cover 37, resulting in discharge of pressurized gas from gas cartridge 21. The discharged gas flows through bore 88 and conduit 93, which is in fluid communication with bore 88 and passes through interconnecting structure 8 from puncture unit housing 18 to housing 96 of pressure regulating unit 24. Sealing elements 22 and 23, e.g. O-rings, at the two ends of bore 88, respectively, prevent gas seepage.

Pointed end 82 may be centered with respect to shaft 87 and head element 89, yet the pressurized gas discharged from gas cartridge 21 is free to exit the opening formed in metallic cover 37 by means of a notched needle tip 91 as shown in FIG. 36. Solid needle tip 91, which may be conical, is configured with a V-notch 94 formed from pointed end 82 to interface 86 with shaft 87 and defining a solid angle of less than 90 degrees, e.g. 45 degrees. The discharged gas flows through V-notch 94, crossing the opening formed in metallic cover 37, to bore 88.

Alternatively, pointed end 82 is positioned off-center with respect to shaft 87 and head element 89, as shown in FIG. 37, although shaft 87 is generally centered with respect to head element 89. To produce this off-center arrangement, shaft 87 is cut at an angle to define the planar surface of needle tip 92 having a sharp peripheral edge, which may be elliptical. Needle tip 92 is one side of a projected triangular configuration that contacts the thin metallic cover 37 of gas cartridge 21 when puncture pin 100 provided with needle tip 92 is viewed from the side as shown in FIGS. 38A-B, with the second side of the triangular configuration being the outer surface 97 of shaft 87. Shaft 87 is of a uniform diameter until a region of puncture pin 100 at which the shaft coincides with the periphery of the needle tip surface. First sharp side 92 and second unsharpened side 97 of the triangular configuration are angularly separated from each other by an angle of less than 90 degrees, e.g. 45 degrees.

As schematically illustrated in FIGS. 38A-B, the opening formed within metallic cover 37 of gas cartridge 21 upon being pierced by pointed end 82 becomes enlarged while puncture pin 100 continues to be longitudinally displaced in the same direction. This opening enlargement is caused by increased tension in metallic cover 37 of gas cartridge 21 due to the corresponding increase in the width of the projected triangular configuration that contacts the metallic cover in a direction away from pointed end 82.

A lateral force is applied to the edge of the pierced opening as the width of the projected triangular configuration between a region longitudinally aligned with pointed end 82 and a region along the peripheral edge of needle tip 92. This applied lateral force results in a peeling action of the thin metallic cover. The resilient peeled portion P associated with metallic cover 37 is in contact with sharp side 92 as the latter cuts into metallic cover 37, resisting efflux from this metallic cover region of pressurized gas, similar to the influence of a sealing element. In contrast, a peeled portion is not produced when shaft outer surface 97 is displaced along the adjoining edge of the opening due to the unchanging distance between a region longitudinally aligned with pointed end 82 and a region along shaft outer surface 97. A small passageway lateral to shaft outer surface 97 is thus formed along which the pressurized gas G is able to infiltrate and to be discharged from gas cartridge 21.

It will be appreciated that the structurally strong puncture pin 100 may be used in conjunction with any embodiment described herein, or for puncturing a gas cartridge in general, even not in relation to a pneumatic tourniquet.

Head element 89 limits the inward displacement of puncture pin 19 upon contacting a surface of the puncture unit housing 18 when set to the displaced position. Puncture pin 19 may be returned to the retracted position by the pressure of the discharged gas when the force applied to the activation handle is released.

Figure 12:
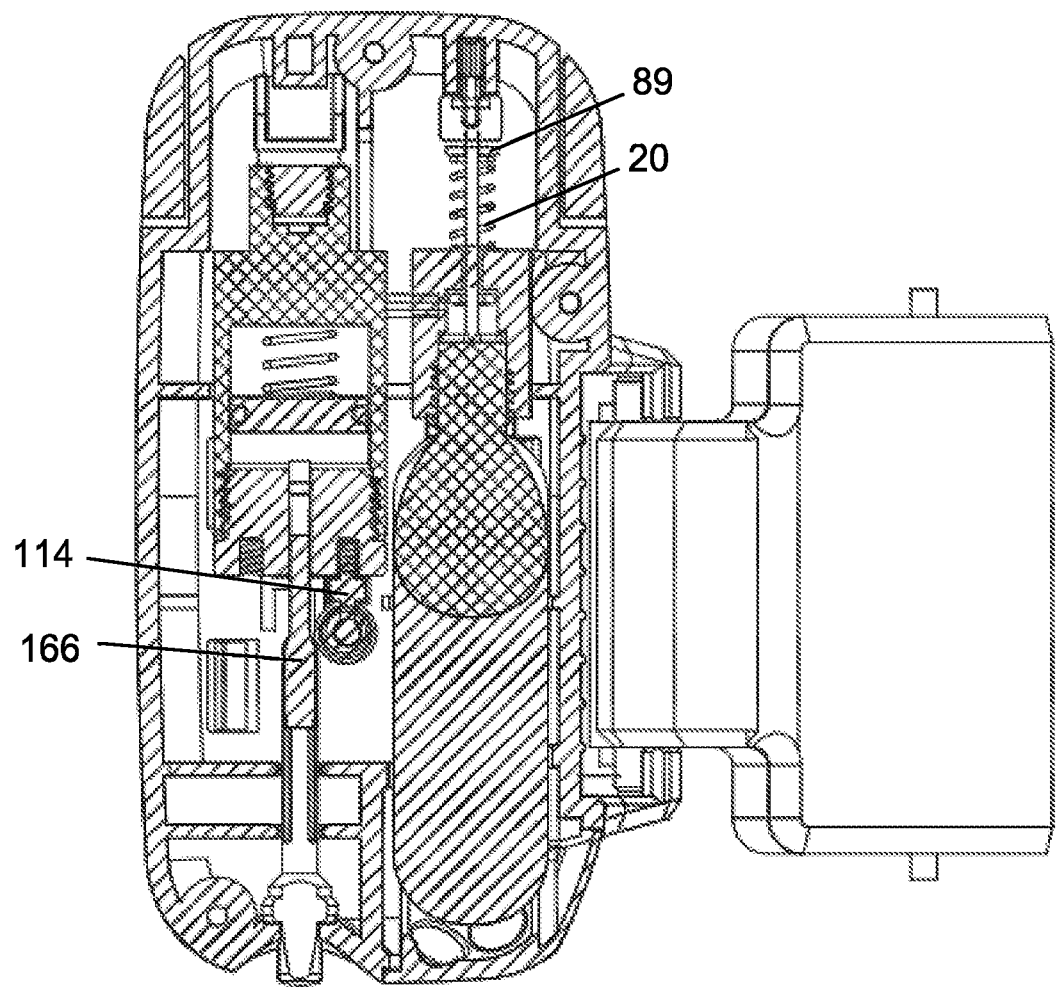
FIG. 12 is a horizontal cross sectional view of another embodiment of a gas flow control assembly, shown without the tube of the pressure regulating unit.

Alternatively, as shown in FIG. 12, a helical spring 20 surrounding the puncture pin shaft is biased to assist in returning the puncture pin to the retracted position after the force applied by the activation handle has been released. Helical spring 20 may be compressed by head element 89, for example simultaneously with the pivoting of the activation handle and the puncturing of the metallic cover. When the force applied to the activation handle is released, the stored spring energy is also released, causing the puncture pin to be retracted. The retracted head element may consequently apply a force that causes the activation handle to pivot in an opposite direction to a non-pivoted position.

Figure 13:
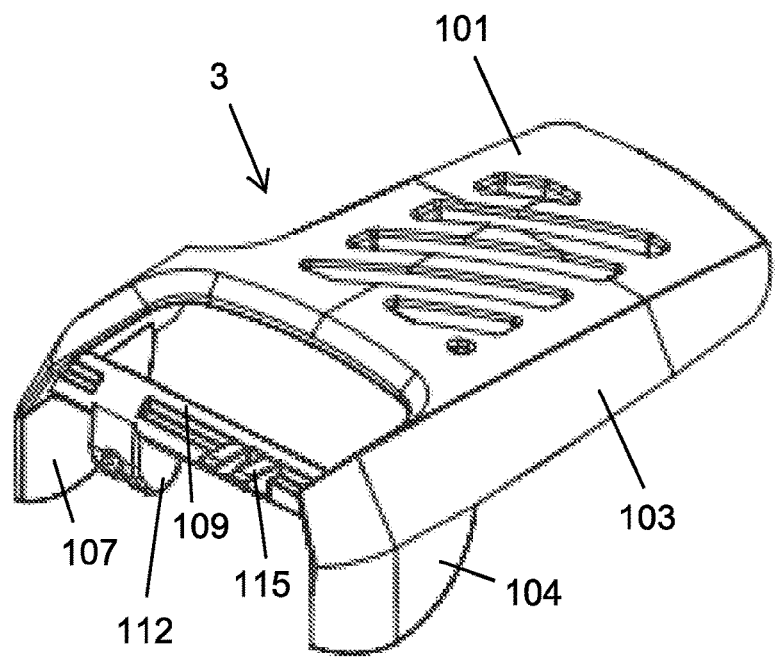
FIG. 13 is a perspective view from the top of an activation handle when separated from the casing of the gas flow control assembly used in conjunction with the tourniquet of FIG. 1.
Figure 14:
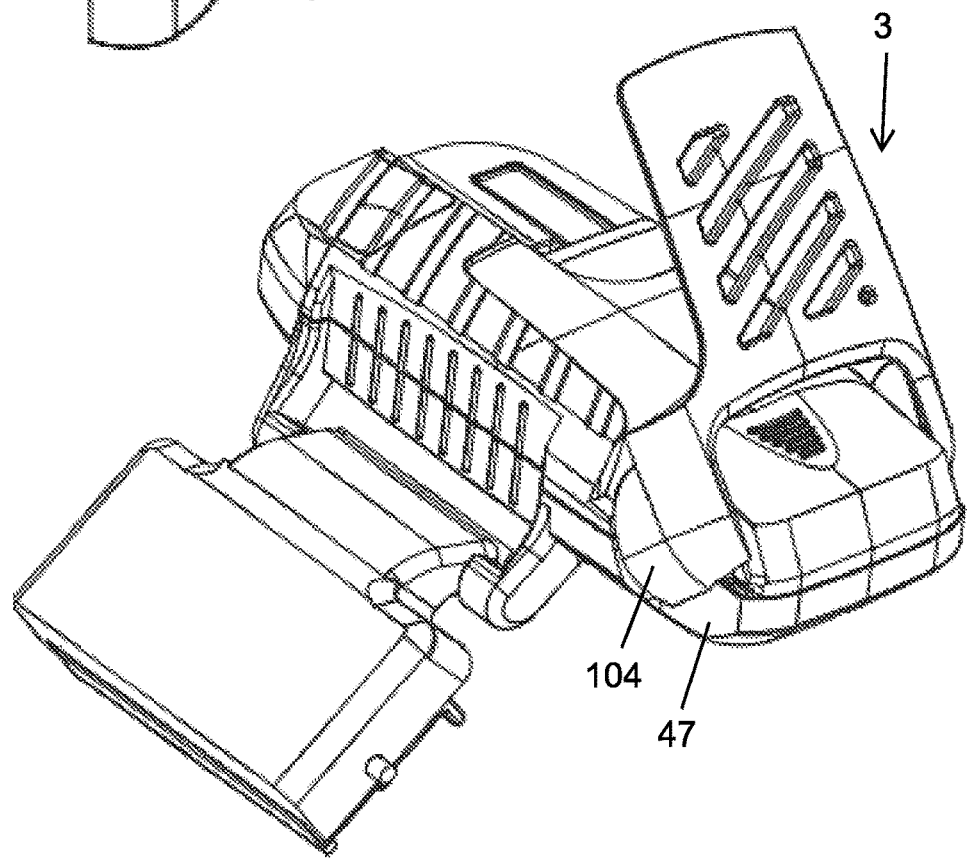
FIG. 14 is a perspective view from the top of the tourniquet of FIG. 1, shown when the activation handle is in a pivoted position.

FIG. 13 illustrates a user friendly activation handle 3 when separated from the casing of the gas flow control assembly. Activation handle 3 comprises a thin and wide-area, substantially planar user-manipulatable surface 101, which may have an arcuate distal edge in order to avoid interference with the casing when being pivoted. User-manipulatable surface 101 is provided with two opposed sidewalls 103 adapted to be contiguous with a corresponding upper casing section sidewall when activation handle 3 is in an unpivoted position and that extend along the entire length of surface 101, or along only a distal portion of surface 101 as shown in FIGS. 1 and 14. An arcuate extension 104 is located below, and curves inwardly at a portion thereof with respect to, the distal region of the corresponding sidewall. A planar surface 107 substantially perpendicular to user-manipulatable surface 101 is in contact inwardly with respect to an extreme distal portion of a corresponding pair of a sidewall 103 and extension 104. A laterally extending beam 109 extends between the two planar surfaces 107, and has a curved surface which is rotatably mounted in two laterally spaced, thin concave seats 28 provided with lower section 38 (FIG. 2), to define the axis of rotation of activation handle 3.

Figure 15:
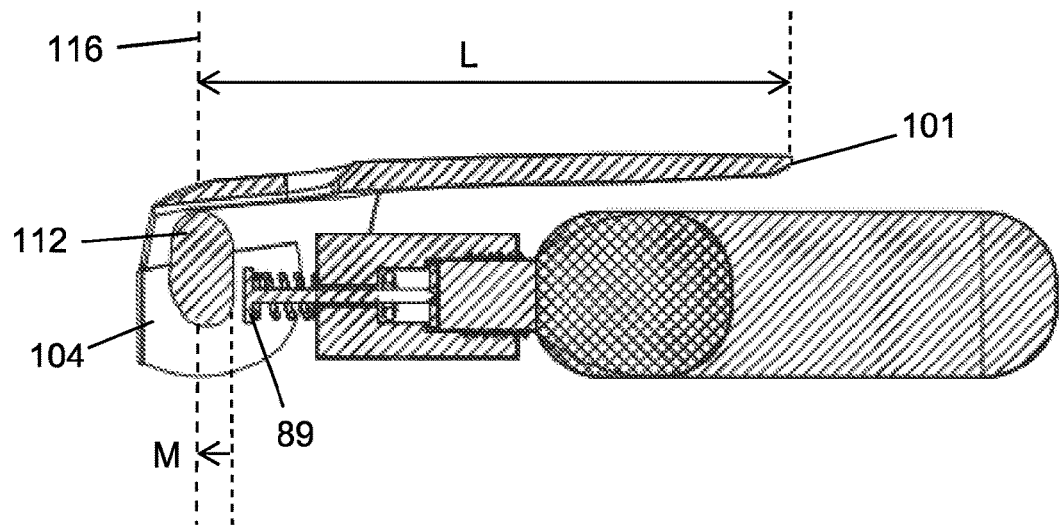
FIG. 15 is a longitudinal cross sectional view cut through a portion of the gas flow control assembly used in conjunction with the tourniquet of FIG. 1, showing the activation handle in a non-pivoted position while a cam associated therewith is in drivable proximity to a head element of the puncture pin.

Protruding downwardly from beam 109 is a cam 112, e.g. elliptically shaped, which is in drivable proximity to head element 89 of the puncture pin, as shown in FIG. 15. One or more stoppers 115, e.g. triangularly shaped, protrude distally from beam 109 in order to limit the pivotal displacement of activation handle 3 by contacting a region of the gas flow control assembly casing.

This configuration of activation handle 3 advantageously provides a mechanical advantage in terms of the ratio of the longitudinal length L of user-manipulatable surface 101 from line 116 passing through its axis of rotation which coincides with beam 109 to the longitudinal length M of cam 112 from the axis of rotation, which ranges from 16-22:1, for example 20:1. With this mechanical advantage, an-average magnitude force applied while raising user-manipulatable surface 101 will output an amplified driving force applied to the puncture pin on the order of 20 kg, which is sufficient to puncture the metallic cover 37 of gas cartridge 21.

Figure 16:
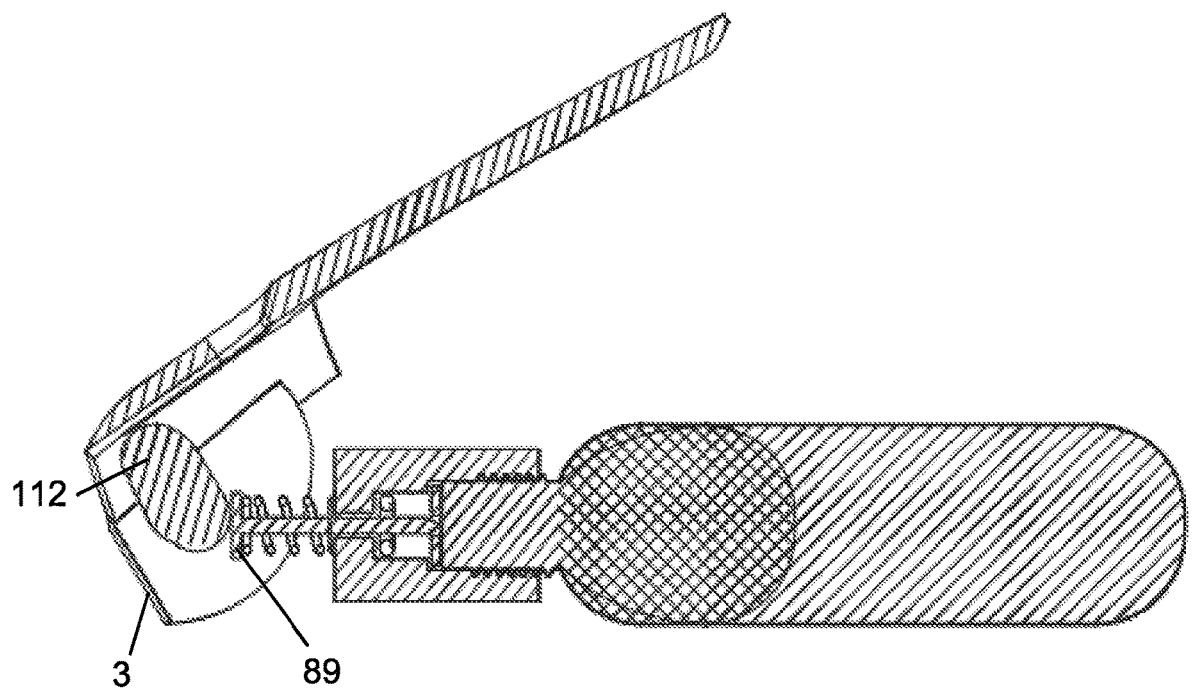
FIG. 16 is a longitudinal cross sectional view cut through a portion of the gas flow control assembly used in conjunction with the tourniquet of FIG. 1, showing the activation handle in a pivoted position.

When activation handle 3 is pivoted about its axis of rotation as shown in FIGS. 14 and 16, cam 112 attached thereto is also pivoted in a similar direction. At this pivoted position, the curved periphery of cam 112 slidingly and drivingly contacts head element 89 to the inwardly displaced position so that the pointed end of the puncture pin punctures the metallic cover. A curved recess 47 formed in the gas flow control assembly casing facilitates the pivoted displacement of arcuate extension 104 without interference. The actions are reversed when activation handle 3 is pivoted in an opposite direction.

The structure and operation of pressure regulating unit 24 will now be described, with reference to FIGS. 6, 7, 11 and 17-20.

Figure 17:
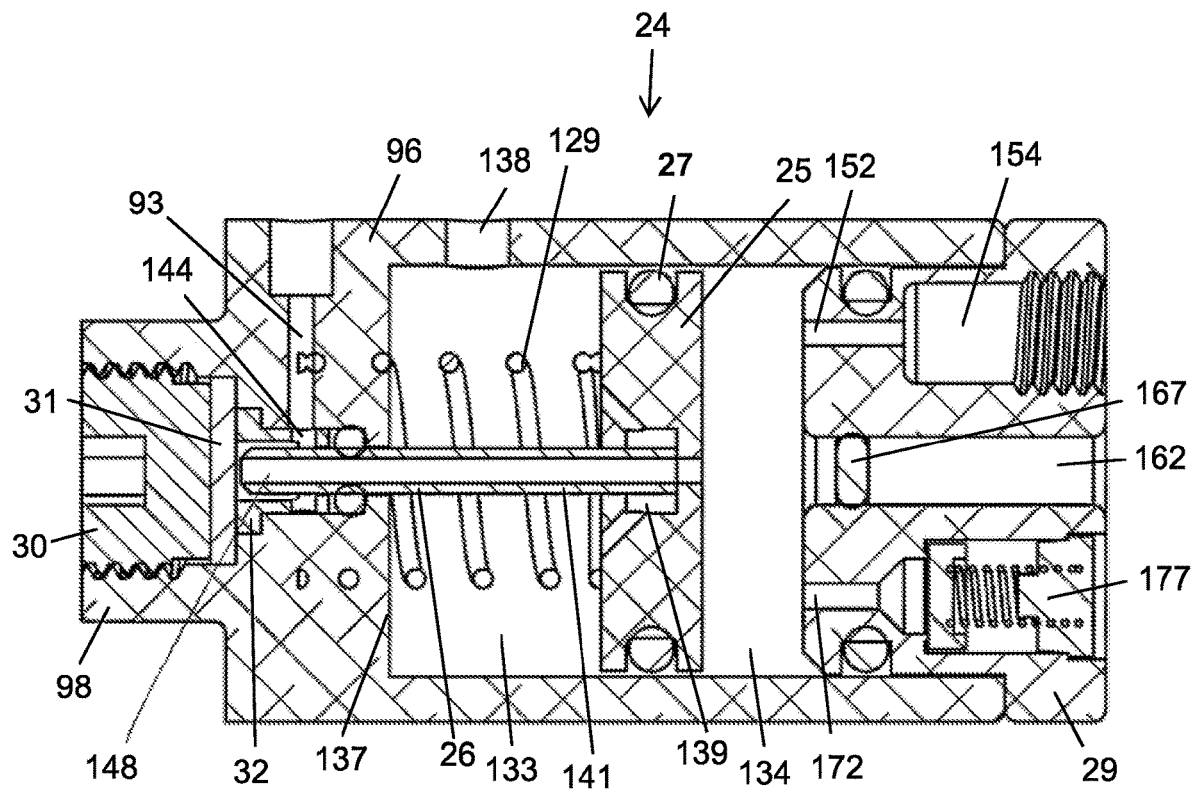
FIG. 17 is an enlargement of a portion of FIG. 11, showing details of the pressure regulating unit.
Figure 18:
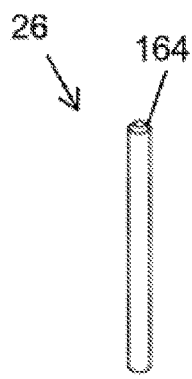
FIG. 18 is a perspective view from the front of a tube usable in conjunction with the pressure regulating unit of FIG. 17.

As shown in FIG. 17, pressure regulating unit 24 has a housing 96 configured with an internal cavity within which piston 25 fitted with O-ring 27, or any other suitable sealing element, is axially and differentially displaceable to define a spring-based supply chamber 133 and a separated regulating chamber 134. Supply chamber 133 is supplied with atmospheric air via opening 138 formed in housing 96.

A narrow hollow tube 26 connected to piston 25, such as by adhesive material 139, or alternatively by a fastener such as a threaded connection, passes through the entire thickness of piston 25 and is in fluid communication with regulating chamber 134. Tube 26 is adapted to receive pressurized gas discharged from the gas cartridge via conduit 93 and to transfer the gas to regulating chamber 134. Helical spring 129, which may be attached to the distal edge 137 of supply chamber 133, surrounds tube 26, and is used to control the pressure within the strap interior.

Cap 30, which may be metallic and threadedly engageable with housing 96 at narrow end 98 thereof, is used to direct the pressurized gas to tube 26. A planar sealing element 31, e.g. made of EPDM rubber, is attached to the proximal end of cap 30, and is also attached to an annular flanged element 32, e.g. planar, configured to carry an elongated annular element 141 within which tube 26 is receivable and axially displaceable. Annular element 141 has two openings 144, which may be diametrically opposite to each other. One of the openings 144 is alignable with conduit 93 when cap 30 is engaged with housing 96 to a fullest extent in conjunction with aligning means well known to those skilled in the art. The discharged pressurized gas is non-escapingly flowable from conduit 93 to the aligned opening 144, and from the aligned opening to the distal end of tube 26, i.e. close to cap 30, by means of various dedicated passageways, such as passageways of varying diameters and orientations, provided within the annular flanged element 32 and elongated element 141. The proximal end of elongated element 141 holds O-ring 27 constituting additional means for preventing the escape of the pressurized gas.

Three secondary passageways 152, 162 and 172 formed in shell 29, which is connected to housing 96, are in fluid communication with regulating chamber 134. First passageway 152 is used for the flow of the pressurized gas to the strap interior. First passageway 152 may be in communication with threadedly engageable socket 154, which is adapted to be engaged, e.g. releasably engaged, with discharge conduit 114 illustrated in FIGS. 7 and 12. Manual pressure release initiator 4 is in communication with second passageway 162. Pressurized gas, if its pressure rises about a predetermined threshold, is releasable to the atmosphere by means of safety valve 177, the structure of which is well known to those skilled in the art, through third passageway 172. Thus the same pneumatic tourniquet may be used for suppressing hemorrhaging while the victim is treated at the emergency setting, flown to the hospital and treated at the hospital without concern that the pressure of the gas will be excessive.

When the pressurized gas is initially discharged from gas cartridge 21, there is an axial clearance between the distal end of tube 26 and sealing element 31 since the atmospheric pressure in supply chamber 133 is greater than or equal to the pressure in regulating chamber 134, which is devoid of pressurized gas, and spring 129 is biased to retain piston at a predetermined spacing from the distal edge 137 of supply chamber 133. Thus the pressurized gas is introduced into tube 26 and flows to regulating chamber 134 via first passageway 152, allowing the pressure within strap interior 53 to rise. Eventually, following the flow of pressurized gas into regulating chamber 134, the pressure in regulating chamber 134 is greater than the pressure in supply chamber 133 and greater than the biasing force of spring 129, and piston 25 is forced to be distally displaced. When piston 25 is sufficiently distally displaced, the distal end of tube 26 is occluded by sealing element 31, preventing additional inflow of pressurized gas. Thus the pressure within strap interior 53 is retained at a predetermined level and sufficient pressurized gas remains in gas cartridge 21 to enable additional hemorrhage suppression operations and to impart the pneumatic tourniquet with the capability of being a multi-use tourniquet.

As opposed to prior art pressure regulators that rely on precise and expensive machining with a CNC lathe in order to achieve reliable sealing, to provide for example a conical tube configuration with a smooth finish and having an outer diameter of at least 6 mm that is formed integrally with the piston, tube 26 advantageously has an outer diameter 148 of less than 2.5 mm. At such a small dimension, tube 26 shown in FIG. 18 can achieve reliable sealing by providing a conical distal end 164 produced by inexpensive cutting and without a smooth finish, since mere contact between the distal end and the sealing element that results in only slight depression of the sealing element is sufficient to reliably occlude tube 26. Other advantages of a small-sized tube include the ability of being mechanically connectable to the piston, quick and inexpensive material removal time as the tube is produced from a blank having a diameter substantially equal to that of the tube rather than that of the integral relatively large-sized piston as has been practiced heretofore in the prior art, a simply produced seal, and a low required sealing force in response to using a small-diameter tube.

The operation of manual pressure release initiator 4 will now be described with reference to FIGS. 6, 12, 17, 19 and 20.

Manual pressure release initiator 4 comprises main rod 166 that is axially displaceable within second passageway 162 of shell 29 and that cooperates with O-ring 167 normally fitted within, and of a substantially equal outer diameter as, the second passageway. A secondary rod 173 extends proximally from, and below, the proximal end of main rod 166, and terminates with a finger-engageable protuberance 176. A stopper 178, e.g. an oblique stopper, extends proximally from the interface between main rod 166 and secondary rod 173, and is used to limit the proximal displacement of manual pressure release initiator 4 upon contacting a casing element 33, as shown in FIG. 7.

Alternatively, the manual pressure release initiator may comprise a single rod extending distally from protuberance 176.

Figure 19:
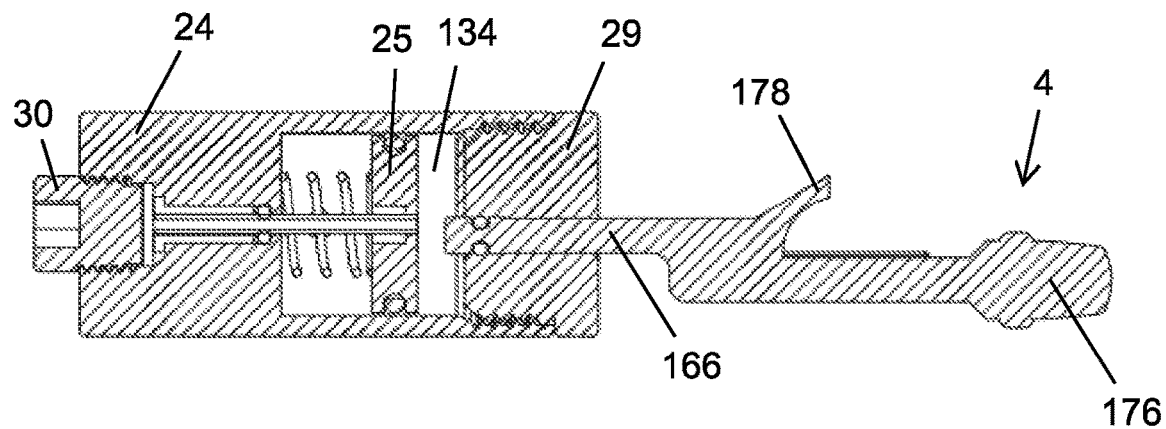
FIG. 19 is a longitudinal cross sectional view cut through a portion of the gas flow control assembly used in conjunction with the tourniquet of FIG. 1, showing the manual pressure release initiator when set to a retracted proximal position.
Figure 20:
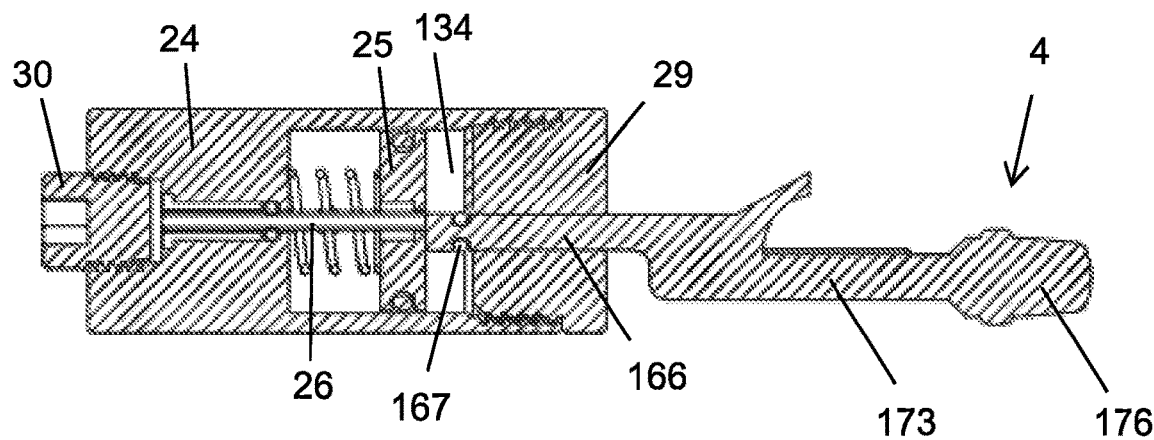
FIG. 20 is a longitudinal cross sectional view cut through a portion of the gas flow control assembly used in conjunction with the tourniquet of FIG. 1, showing the manual pressure release initiator when set to an advanced distal position.

FIGS. 12 and 19 illustrate manual pressure release initiator 4 when set to a retracted proximal position. At this retracted position, main rod 166 is received within, and engaged with, O-ring 167 which is sealingly engaged within second passageway 162, such that the second passageway is occluded in unison by main rod 166 and O-ring 167 to prevent egress of the pressurized fluid received in regulating chamber 134 to the atmosphere.

If the medical practitioner desires to reduce the pressure within the strap interior in order to remove the tourniquet from the victim or to prevent development of ischemia within muscle tissues during prolonged use of the tourniquet, protuberance 176 is pushed to cause distal displacement of main rod 166 together with O-ring 167 engaged therewith. When main rod 166 is set to the distal advanced position illustrated in FIG. 20, O-ring 167 is displaced outwardly from second passageway 162 and into regulating chamber 134, producing a radial clearance between main rod 166 and the wall of second passageway 162. When main rod 166 is distally advanced to a fullest extent, it contacts piston 25 and causes the distal end of tube 26 to be occluded by sealing element 31. Since the distal end of tube 26 is occluded, ingress of pressurized gas into regulating chamber 134 is prevented and egress of the fluid received in regulating chamber 134 to the atmosphere via the radial clearance around main rod 166 commences, to enable reduction in the magnitude of the hemorrhage suppressing force being applied by the fluid pressure within the strap interior. The magnitude of the hemorrhage suppressing force may be periodically reduced during short intervals of e.g. 10-15 min.

The degree of pressure reduction may be simply controlled by releasing the force applied to protuberance 176. After the force applied to protuberance 176 is released, the pressurized gas remaining in the strap interior flows through first passageway 152 and causes piston 25 to remain distally advanced. Eventually, main rod 166 becomes separated from piston 25 and is subsequently proximally displaced within second passageway 162. Main rod 166 carries O-ring 167 and causes the latter to be received once again within second passageway 162 to occlude the radial clearance.

If all the pressurized gas is allowed to escape to the atmosphere, supply chamber 133 and regulating chamber 134 will achieve equilibrium conditions and the distal end of tube 26 will cease to be occluded by sealing element 141. Thus an additional amount of pressurized gas will be delivered to regulating chamber 134.

The ability unknown heretofore of periodically deflating the strap interior at a pre-hospital setting has significant clinical advantages by being able to prevent the onset of ischemia despite prolonged use of a pneumatic tourniquet. The physician accompanying the wound victim to the hospital is able to monitor his or her physiological conditions, to avoid manifestation of complications such as metabolic changes, reperfusion syndrome and cardiac arrest.

In addition, when protuberance 176 is secured to the distal advanced position by means of a locking device movably connected to the casing of the gas flow control assembly, the distal end of tube 26 will remain indefinitely occluded, allowing the pressurized gas remaining in the gas cartridge to be used for additional hemorrhage suppression operations with respect to other wound victims, following replacement of the inflatable strap.

Figure 21:
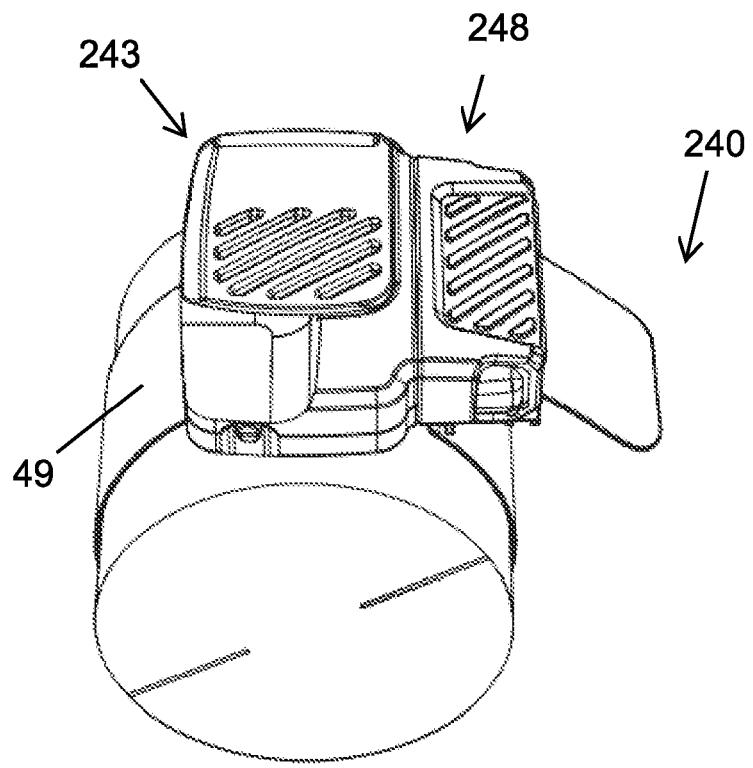
FIG. 21 is a perspective view from the top of another embodiment of a pneumatic tourniquet, shown when deployed on a schematically illustrated wounded limb and the constricting device is coupled with the gas flow control assembly.
Figure 22:
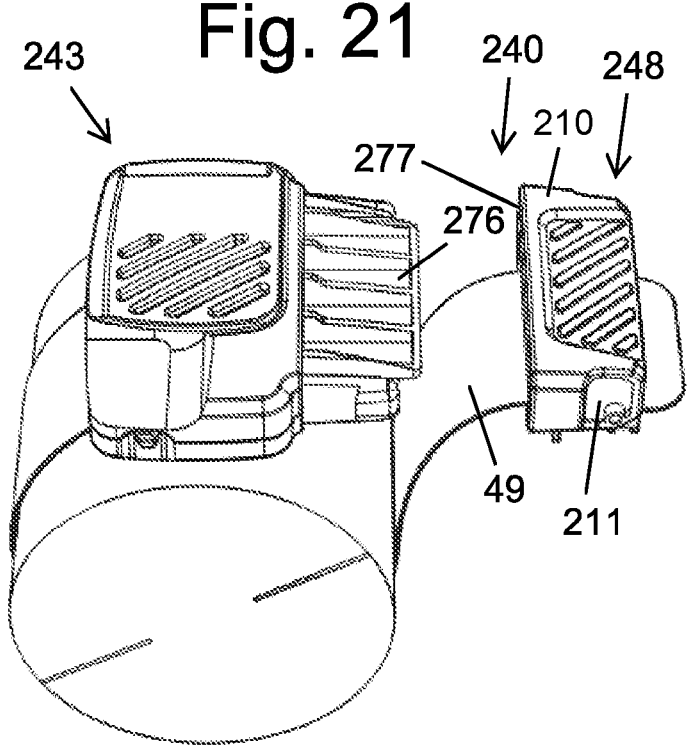
FIG. 22 is a perspective view from the top of the tourniquet of FIG. 21, shown when deployed on a schematically illustrated wounded limb and the constricting device is separated from the gas flow control assembly.

FIGS. 21 and 22 illustrate another embodiment of a pneumatic tourniquet 240 which may be compactly stored by means of a plurality of spaced prongs 276 extending laterally from gas flow control assembly 243. Prongs 276 are insertable in, and connectable to, socket 277 provided with housing member 210 of non-pivoting constricting device 248. Socket 277 is sized to permit connection with prongs 276, yet permit the feeding of inflatable strap 49 therebelow along the strap-engageable surface of rocker 211. The prongs 276 are pressed together in order to release gas flow control assembly 243 from constricting device 248. The operation of gas flow control assembly 243 and of constricting device 248 is identical to that of gas flow control assembly 43 and constricting device 48, respectively, of FIG. 1.

Figure 23:
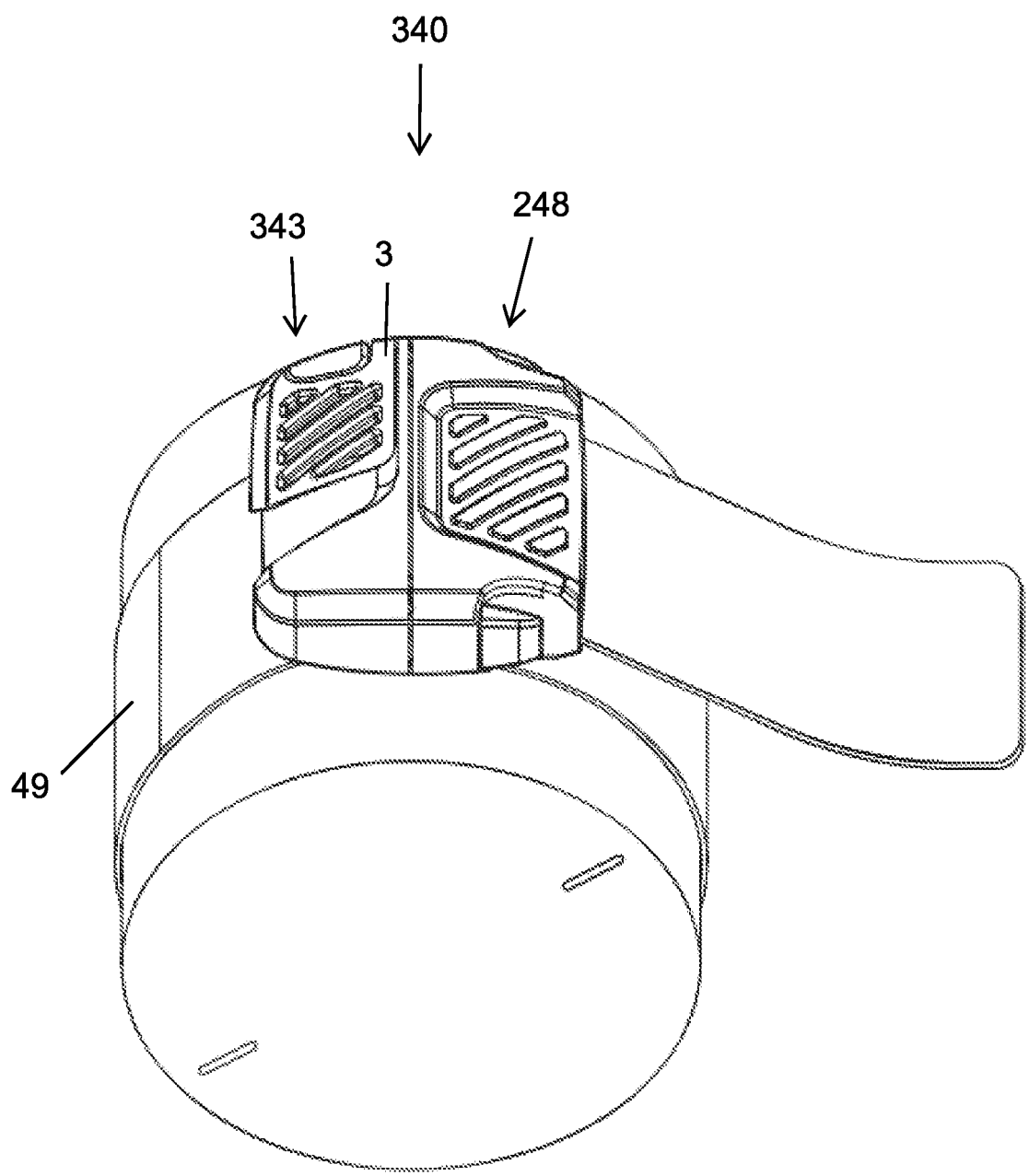
FIG. 23 is a perspective view from the top of another embodiment of a pneumatic tourniquet, shown when deployed on a schematically illustrated wounded limb and the constricting device is coupled with the gas flow control assembly.

FIG. 23 illustrates another embodiment of a pneumatic tourniquet 340 comprising constricting device 248 as described in FIG. 22 and a gas flow control assembly 343 lacking a pressure regulating unit to achieve a more compact configuration. Gas flow control assembly 343 comprises the same structure of activation handle 3 for initiating inflation of strap 49, puncture unit housing 18 within which gas cartridge 21 is releasably couplable, and puncture pin 19 for puncturing the metallic cover normally sealing the gas cartridge as described above with respect to FIGS. 11 and 13. Connection section 46 shown in FIG. 7 may be used for attachment of strap 49 to the gas flow control assembly casing. The flow of pressurized gas discharged from the gas cartridge may be directed to an internal chamber in fluid communication with a safety valve 177 shown in FIG. 17 prior to flowing to the interior of the inflatable strap to prevent occurrences of excessively high pressure.

A plurality of spaced prongs 276 (FIG. 22) extending laterally from gas flow control assembly 343 are insertable in, and connectable to, socket 277 provided with housing member 210 of constricting device 248 to achieve compact storage. The prongs 276 are pressed together in order to release gas flow control assembly 343 from constricting device 248.

Another embodiment of a pneumatic tourniquet 440 is illustrated in FIGS. 24-30.

Figure 24:
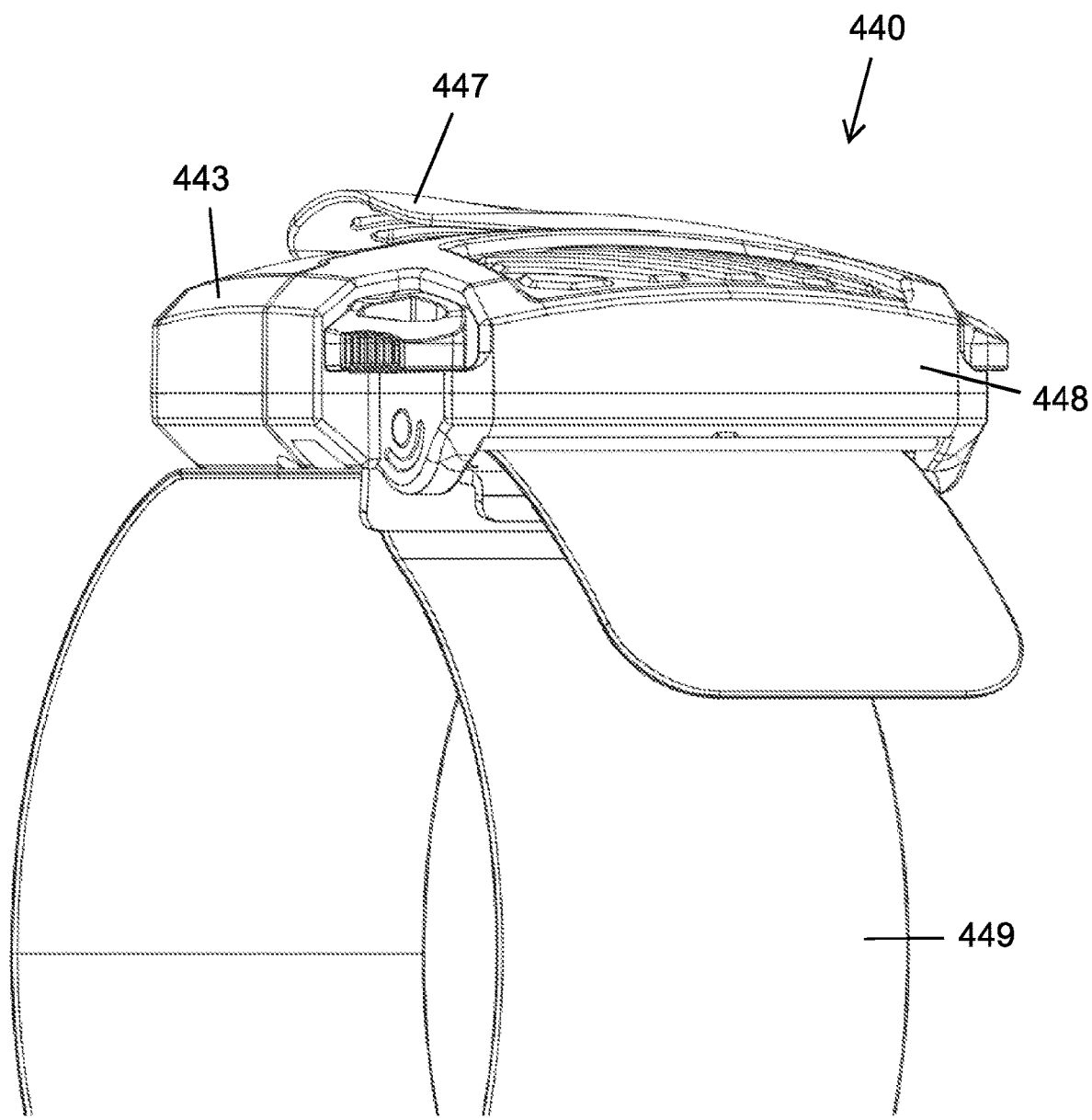
FIG. 24 is a perspective view from the side of another embodiment of a pneumatic tourniquet pre-fed with an inflatable strap.

As shown in FIG. 24, pneumatic tourniquet 440 comprises gas flow control assembly 443 provided with user friendly activation handle 447, non-pivoting constricting device 448 connectable with gas flow control assembly 443, for example as shown in FIG. 23 to provide a compact housing without a pressure regulator, and inflatable strap 449 which is connected to gas flow control assembly 443 and is selectively clamped by constricting device 448. In this embodiment, inflatable strap 449 is configured without an internal sealing layer; however, passage of the pressurized gas from a clamping edge associated with constricting device 448 to the free end of the strap is prevented by an external sealing element, as will be described hereinafter.

It will be appreciated that inflatable strap 449 may also be configured with an internal sealing layer and that pneumatic tourniquet 440 may be configured with a pressure regulator.

Figure 25:
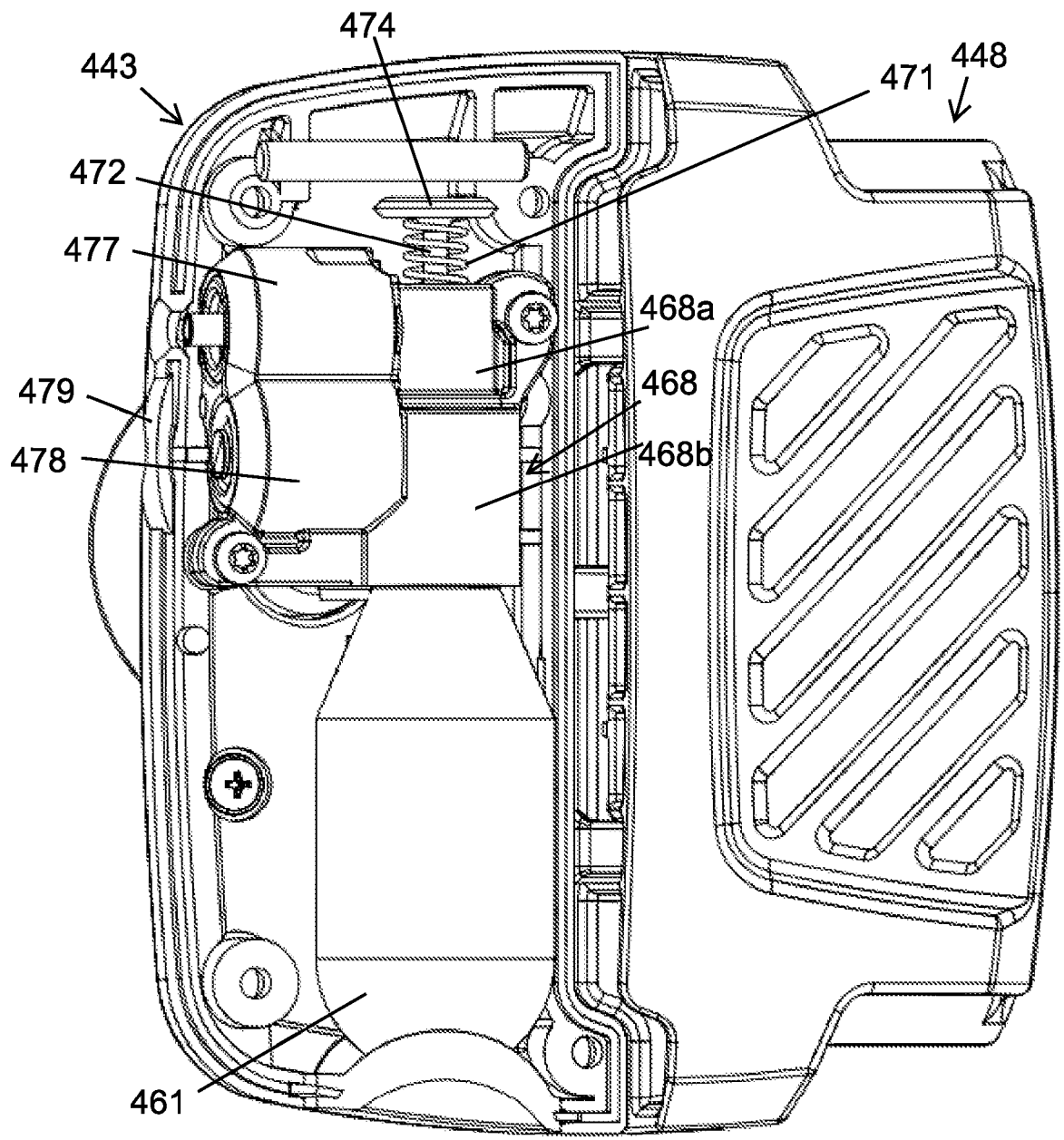
FIG. 25 is a top view of the tourniquet of FIG. 24, shown when an upper casing of the gas flow control assembly is removed.

FIG. 25 illustrates another embodiment of a gas flow control assembly. Gas flow control assembly 443 is shown to be positioned in abutting relation with constricting device 448, when the activation handle is removed. Gas cartridge 461, which is equipped with a valve actuator to initiate the discharge of gas, is shown to be releasably coupled such as by a threaded connection within a piston housing 468, e.g. made of two differently sized sections 468a and 468b. An elongated activation piston 472 at a non-activated position protrudes through an opening of piston housing section 468a, such that its head 474 is spaced from a laterally extending axle 476 (FIG. 29), i.e. relative to the longitudinal axis of gas cartridge 461, about which the activation handle is able to rotate. After activation, activation piston 472 is returned to the non-activated position by spring 471.

Gas flow control assembly 443 may also comprise means for adjusting the gas pressure within the strap interior. A pressure release valve 477 for manual release of the internal strap pressure, for example by slow and controlled release of pressure prior to removal from the subject, may be operatively connected to piston housing section 468a. A pressure control mechanism 478 for automatic regulation of the internal strap pressure during deployment of the pneumatic tourniquet may be operatively connected to piston housing section 468a by a conduit. Pressure control mechanism 478 may have a selector 479 by which a user is able to select the pressure to be set.

Figure 26:
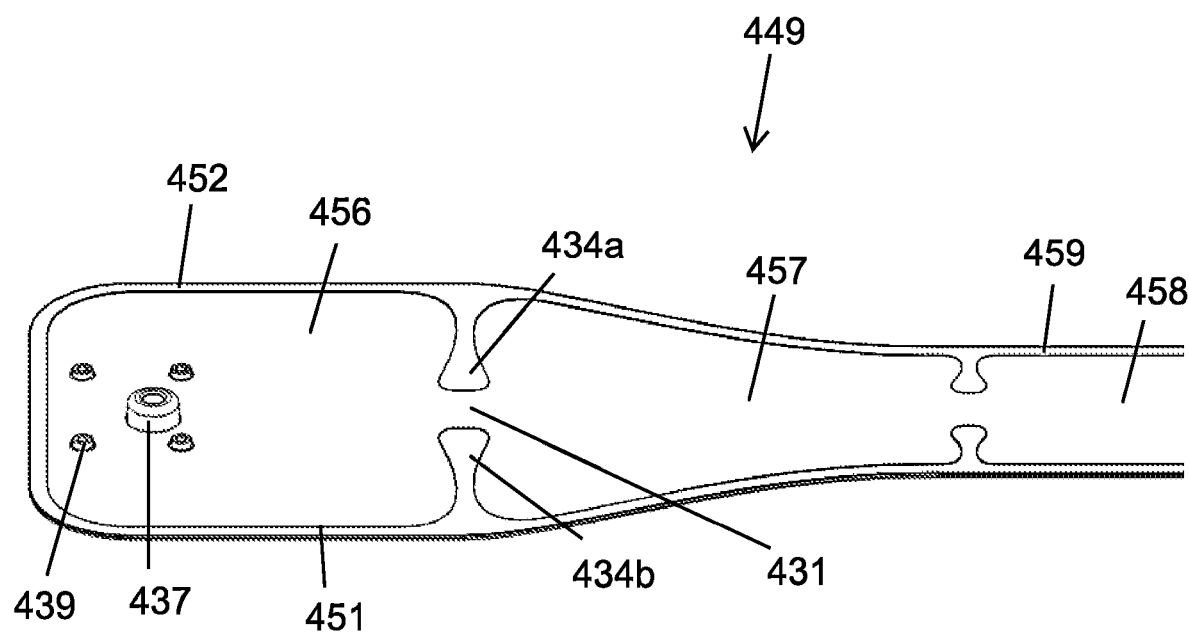
FIG. 26 is a perspective view from the top of a portion of an inflatable strap used in conjunction with the tourniquet of FIG. 24.

As shown in FIG. 26, inflatable strap 449 having two different widths may be configured with a plurality of serially interconnected cells, such as cells 456-458, adapted to help reduce the volume in the strap interior that is able to be inflated, so that a reduced volume of pressurized gas, relative to a pneumatic strap lacking serially interconnected cells, is needed in order to transmit a sufficient hemorrhage suppressing force to the wounded limb. Each of cells 456-458 is attached to an outer, lengthwise extending border layer 451 of strap 449.

A plurality of identical and serially interconnected cells 458 may be provided at the narrow-width section 459. Cell 456 is provided at the wide-width connection section 452, and transitional cell 457 having a change in width is interposed between cell 452 and the cell 458 that is closest to cell 456. A short lengthwise extending neck portion 431 extends between two adjacent cells, to facilitate flow of pressurized gas between one cell to another. Two widthwise protrusions 434a and 434b, e.g. tooth-shaped, extend from opposite sides of a corresponding region of border layer 451 to delimit the corresponding neck portion 431 and adjoining surfaces of the adjacent cells, generally curved. Inlet port 437 through which pressurized gas flows to the strap interior protrudes inwardly through the upper wall of cell 456, and fastening means 439 surrounding inlet port 437 for connection to the gas flow control assembly casing protrude upwardly from cell 456. Each fastening means 439 may be a snapping fastener or other connection means well known to those skilled in the art, whether releasable or inseparable means, and may be spaced from inlet port 437 by a different distance. Alternatively, all fastening means may be equidistantly spaced from inlet port 437.

FIGS. 27A-B illustrate top and side views, respectively, of strap 449 when inflated and unconnected with the gas flow control assembly. In addition to wide-width cell 456 and transitional cell 457, strap 449 is configured with a plurality of narrow-width cells 458a-e, through the adjoining neck portion 431 of each cell pressurized gas is able to flow from inlet port 437 in order to inflate strap 449. A partition 467 adjoining cell 458e and terminal cell 462 prevents the flow of pressurized gas to terminal cell 462, ensuring that the uninflated terminal cell 462 will be of a minimal thickness so as to be comfortable to the subject when the remaining portions of strap 449 are wrapped about a limb of the subject and inflated. Of course, additional portions of inflated strap 449 adjoining terminal cell 462 that distally protrude from the clamping edge of the constricting device may be uninflated when the pressurized gas is prevented by the clamping edge from flowing to these additional portions.

Each cell is delimited by the external surface 453 and limb facing surface 454 of strap 449 and by the widthwise protrusions 434 embedded in each of external surface 453 and limb facing surface 454. When strap 449 becomes inflated, the widthwise protrusion of external surface 453 becomes separated from the corresponding widthwise protrusion of limb facing surface 454 to form a pyramidal protrusion 434'. The apex of the pyramidal protrusion 434' protruding from the side of external surface 453 meets the apex of a corresponding pyramidal protrusion 434' protruding from the side of limb facing surface 454 at the lengthwise extending weld line 481, which is the connecting interface between external surface 453 and limb facing surface 454.

Figure 27C:
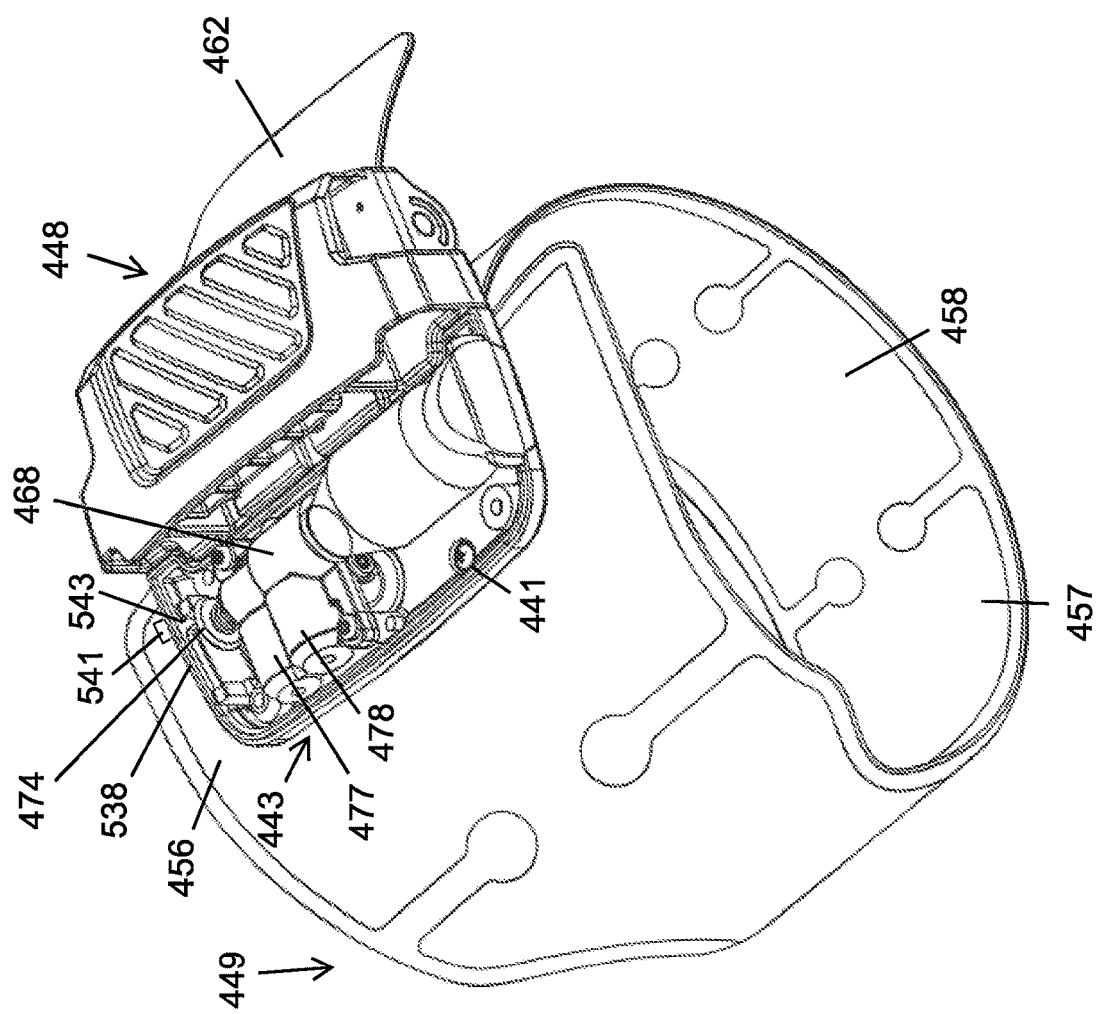
FIG. 27C is a perspective view of the strap of FIG. 27A when connected with the gas flow control assembly and its free end is pre-fed through the constricting device.

FIG. 27C illustrates strap 449 when wide-width cell 456 is connected with gas flow control assembly 443 and the free end 462 of the strap is pre-fed through constricting device 448. A screw 441 passing through an aperture 501 formed in attachment plate 506 of lower casing 538 (FIG. 33) is shown, and is coupled with corresponding fastening means. A screw 441 likewise may pass through an aperture formed in underside surface 41 of FIG. 4 in order to be coupled with corresponding fastening means. The plurality of narrow-width cells 458 extend circumferentially to constricting device 448.

Figure 28A:
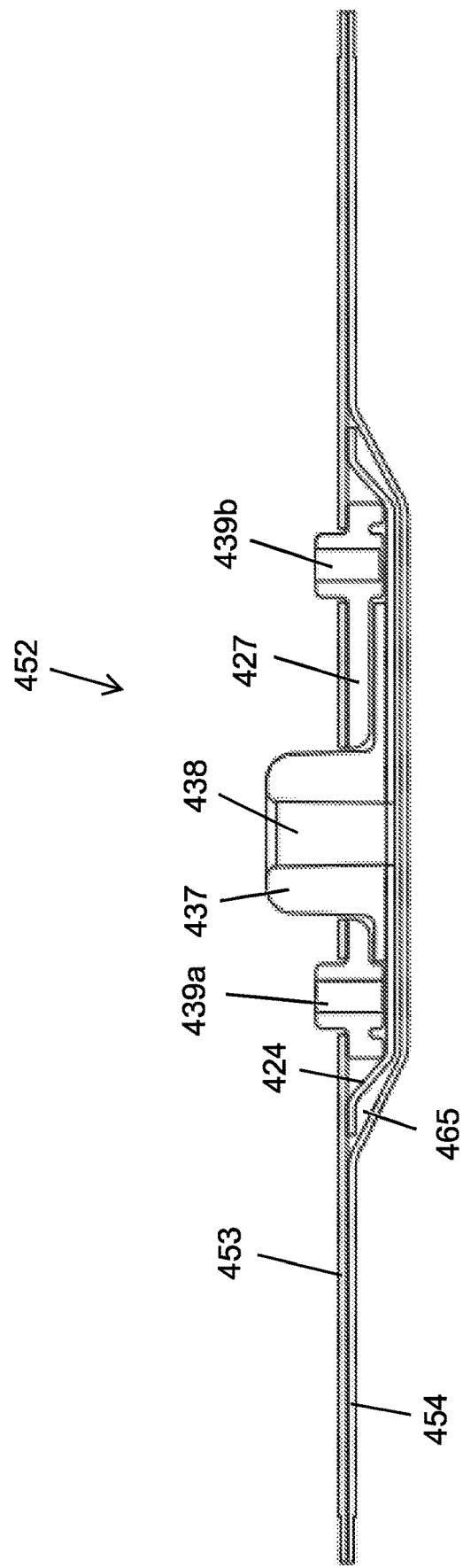
FIG. 28A is a cross-sectional view of the wide-width connection section of FIG. 26.

FIG. 28A illustrates a cross-sectional view of connection section 452. Flexible inlet port 437 protrudes through external layer 453 of the inflatable strap, and its central passageway 438 is in fluid communication with the strap interior 465 which is located between external layer 453 and limb contactable layer 454 of the inflatable strap. In order to reduce the stress concentrations to which connection section 452 is exposed, a semi-rigid sealing layer 424, e.g. made of polyurethane, thermoplastic polyurethane (TPU), or similar materials, which is formed with an aperture, is attached to both inlet port 437 and external strap layer 453, such as by high frequency soldering. The thickness of semi-rigid sealing layer 424 may range from 0.1-0.5 mm, e.g. 0.2 mm. With the exception of the aperture provided to accommodate the inlet port, semi-rigid sealing layer 424 is pinhole free. Inlet port 437 also protrudes through a rigid plastic plate 427 also attached to semi-rigid layer 424, e.g. made of HOPE and polypropylene, from which protrudes a plurality of fastening means, e.g. fastening means 439a-b.

For example, as shown in FIGS. 28B-D, inlet port 437 is configured with a mounting element 435 for attachment to semi-rigid layer 424. Rigid plate 427 is configured with an aperture 426 for receiving inlet port 437 and with four bosses 428, each of which connectable with a fastener, e.g. a screw, passing through a corresponding hole formed in an attachment plate of the gas flow control assembly casing. External strap layer 453 in turn is formed with four apertures 463 to accommodate the bosses 428, respectively, and with a central aperture 466 to accommodate inlet port 437. Following assembly, connection section 452 appears as shown in FIG. 26.

Prior art means for connecting an inflatable strap to a gas flow control assembly generally include a single threaded connection with a valve core. This single connection produces a relatively high stress concentration during deployment of the pneumatic tourniquet while the inflated strap of a relatively high pressure is being wrapped about a wounded limb and applies a relatively high tensile force to the single threaded connection. Many times, pinholes, or small punctures, develop in the strap due to the high stress concentration, resulting in a reduction of the interior strap pressure and wastage of the pressurized gas. The development of high stress concentration at the connection of the inflated strap is exacerbated when the pneumatic tourniquet provides added features found in the present invention such as the pivotable activation handle, constricting device, safety release valve, and self-regulating pressure control mechanism, which, when operated generate vibratory forces that add to the stress concentration.

The relatively high stress concentration is advantageously significantly reduced by use of connection section 452, by which the inflatable strap is connected to gas flow control assembly casing by a plurality of connections, rather than by a single connection. Inlet port 437 is coupled, e.g. releasably coupled, with a nipple 511 protruding from rigid attachment plate 506 (FIG. 33) of the gas flow control assembly casing and being a part of piston housing 468 (FIG. 27C), or is otherwise accessible to the attachment plate, and the attachment plate is additionally securely secured to connection section 452 by the plurality of fastening means. When the strap is inflated, inlet port 437 is pressed against attachment plate 506, and additional pressurized gas is able to flow freely from the gas cartridge to strap interior 465. Semi-rigid sealing layer 424 provides added protection against efflux of pressurized gas from connection section 452.

Figure 29:
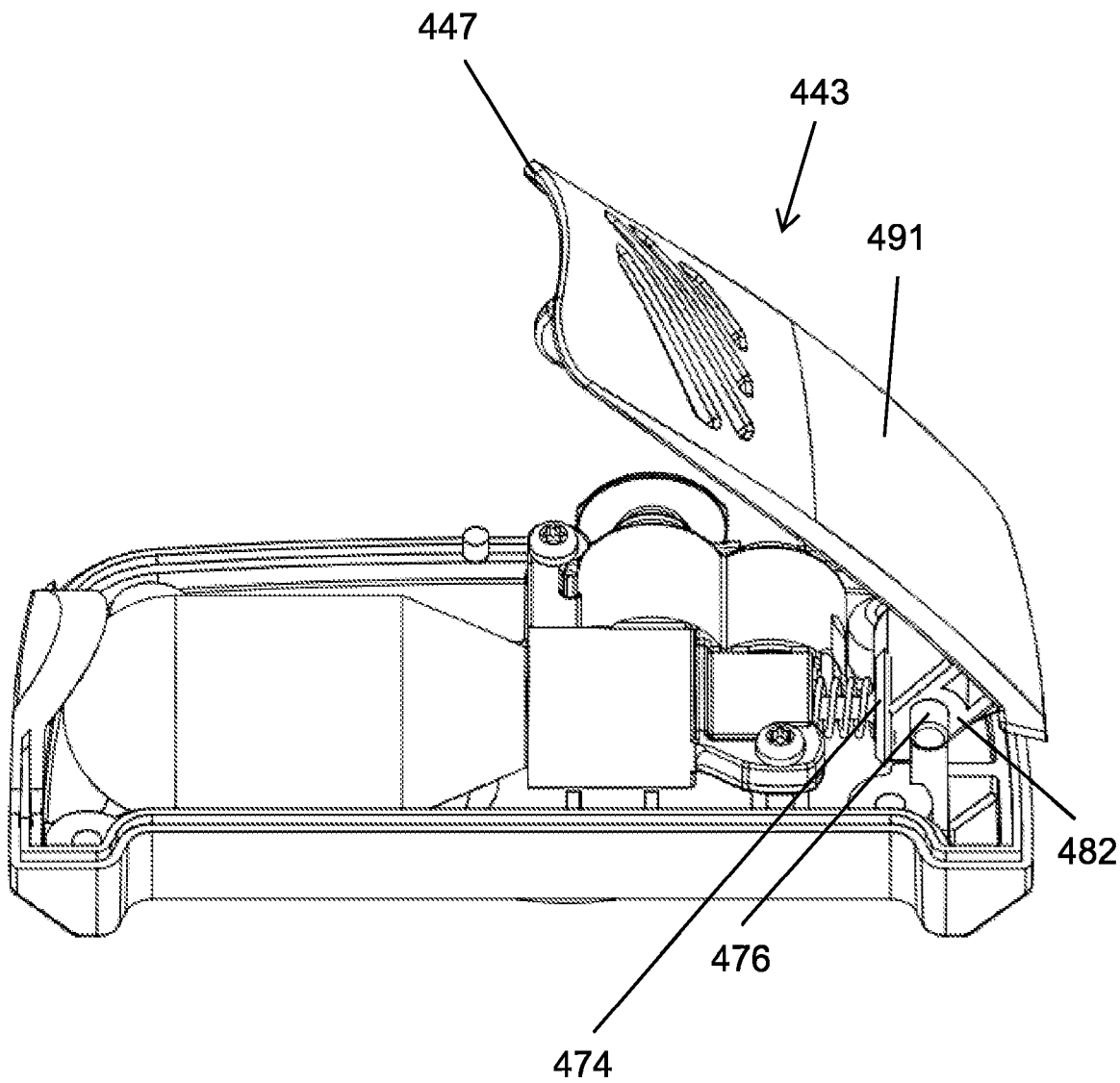
FIG. 29 is a perspective view from the side of the gas flow control assembly of FIG. 24 when separated from the constricting device and the activation handle is set to a pivoted position.

FIG. 29 illustrates gas flow control assembly 443 when activation handle 447 is set to a pivoted position. Two laterally spaced, elongated and narrow mounting elements 482, which are substantially perpendicular to substantially planar user-manipulatable surface 491, are rotatably mounted on axle 476 to facilitate the pivotal displacement of activation handle 447. The end of one of the mounting elements 482 is shown to be in force transmitting relation with activation piston head 474.

Figure 31:
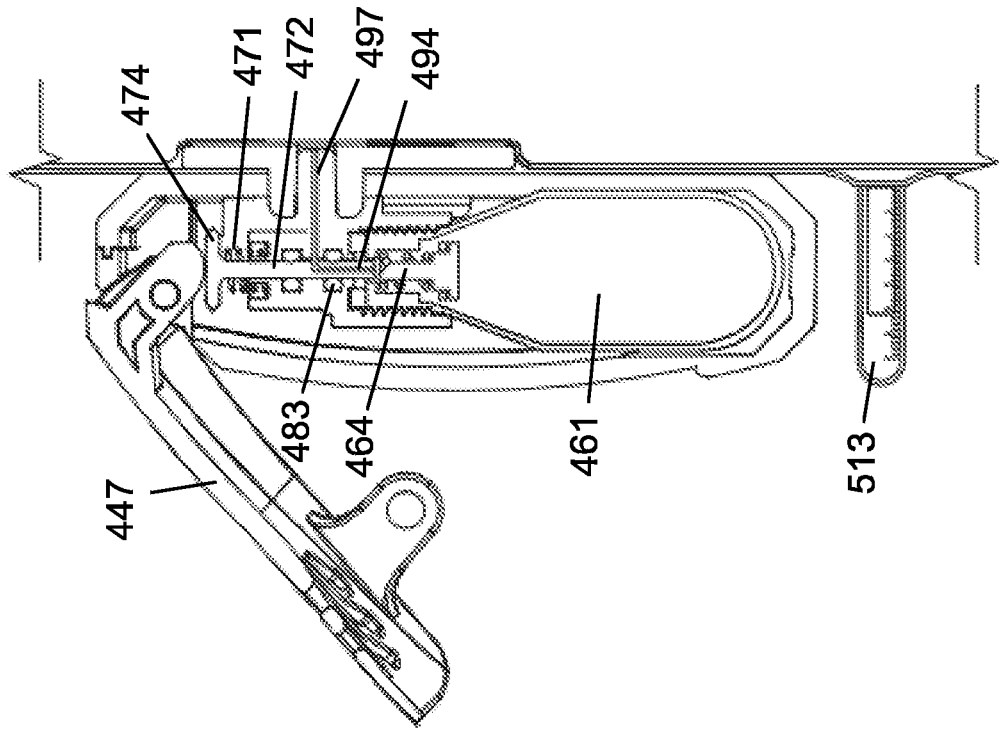
FIG. 31 is a cross sectional view of the gas flow control assembly of FIG. 24, when the activation handle is in a pivoted position and the activation piston is set at an activated position.
Figure 30:
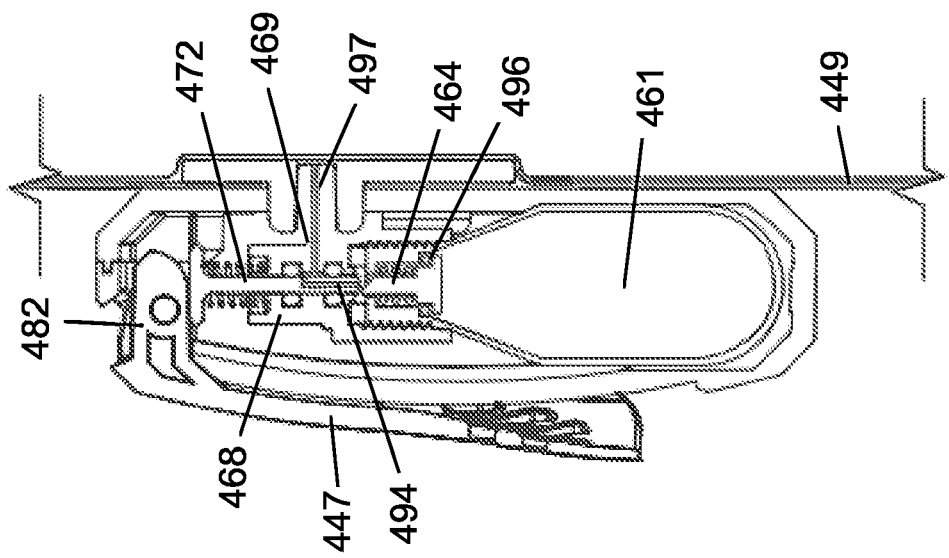
FIG. 30 is a cross sectional view of the gas flow control assembly of FIG. 24, when the activation handle is in a non-pivoted position and the activation piston is set at a non-activated position.

FIGS. 30-31 illustrate the operation of activation piston 472, which functions as a force transmitting element, when cooperating with activation handle 447. Activation piston 472 is longitudinally guided within a longitudinal slot formed in piston housing 468 (not shown). Activation piston 472 carries an angled conduit 494.

In FIG. 30, activation handle 447 is in a non-pivoted position and activation piston 472 is set at the non-activated position while a side edge of a mounting element 482 is in abutting relation with activation piston head 474. The distal end of activation piston 472 is slightly spaced from the valve stem 464 of gas cartridge 461, which is shown to be in a protruding position. At the non-activated position of activation piston 472, the short transversally extending portion of conduit 494 is unaligned with a conduit 497 fixed to a discharge port 469 of piston housing 468 and extending through the inlet port of inflatable strap 449, only a portion of which is illustrated, to prevent inflation of the strap due to leakage of the pressurized gas. Leakage of the pressurized gas from gas cartridge 461 is also prevented by means of annular seal 496 fixed to the base of valve stem 464, also during periods of non-use. Conduit 497 is spaced by a very small clearance from activation piston 472.

In FIG. 31, activation handle 447 is pivoted and transmits the activation force to activation piston 472 via head 474 while spring 471 fixed to a recessed portion of the piston housing becomes compressed. Activation piston 472 is consequently longitudinally displaced until the short transversally extending portion of conduit 494 becomes aligned with conduit 497. Valve stem 464 is consequently contacted by activation piston 472 and is caused to become retracted, so that the valve seat will be uncovered and pressurized gas will flow from the interior of gas cartridge 461 via the valve seat to conduit 494. Since conduit 494 is aligned with conduit 497, the pressurized gas will also flow to the strap interior via the inlet port. A plurality of annular seals 483 surrounding conduit 494 prevent leakage of gas from the abutment region between conduit 494 and conduit 497. In one embodiment, a visually distinctive, schematically illustrated pressure gauge 513 in fluid communication with the strap interior is indicative when the strap interior becomes inflated. In another embodiment, the user will terminate the inflation of pressurized gas into the strap interior in response to an audible reaction generated by the pressure control mechanism 478 (FIG. 27C) when gas is released therefrom.

Upon release of the activation force, the spring force of spring 471 surrounding activation piston 472 is released to urge activation handle 447 to the non-pivoted position and conduit 494 to become unaligned with conduit 497, as shown in FIG. 30. Also, the spring surrounding valve stem 464 ceases to be compressed, and the valve stem returns the protruding position.

Alternatively, activation piston 472 may be longitudinally driven by means of a button 541, or any other actuator, protruding from lower casing 538 of gas flow control assembly 443, as shown in FIG. 27C. Upon transmission of the activation force, a movable rod 543 connected to, or in force transmitting relation with, button 541 is longitudinally driven to proximally displace activation piston head 474. The operation of the activation piston is as described above.

It will be appreciated that activation piston 472 may be used to drive puncture pin 19 shown in FIG. 11.

The pressurized gas discharged from gas cartridge 461 following transmission of the activation force may be in fluid communication with pressure release valve 477 and pressure control mechanism 478 by means of corresponding conduits also fixed to piston housing 468. Conduit 494 carried by activation piston 472 may be configured with additional angled portions, each of which is alignable with a corresponding conduit similar to the manner shown in FIG. 31 following transmission of the activation force. In order to provide the desired pressure control function, each of the corresponding conduits may be equipped with a valve or other pressure biasing mechanism, and optionally with a sealing element.

Figure 32A:
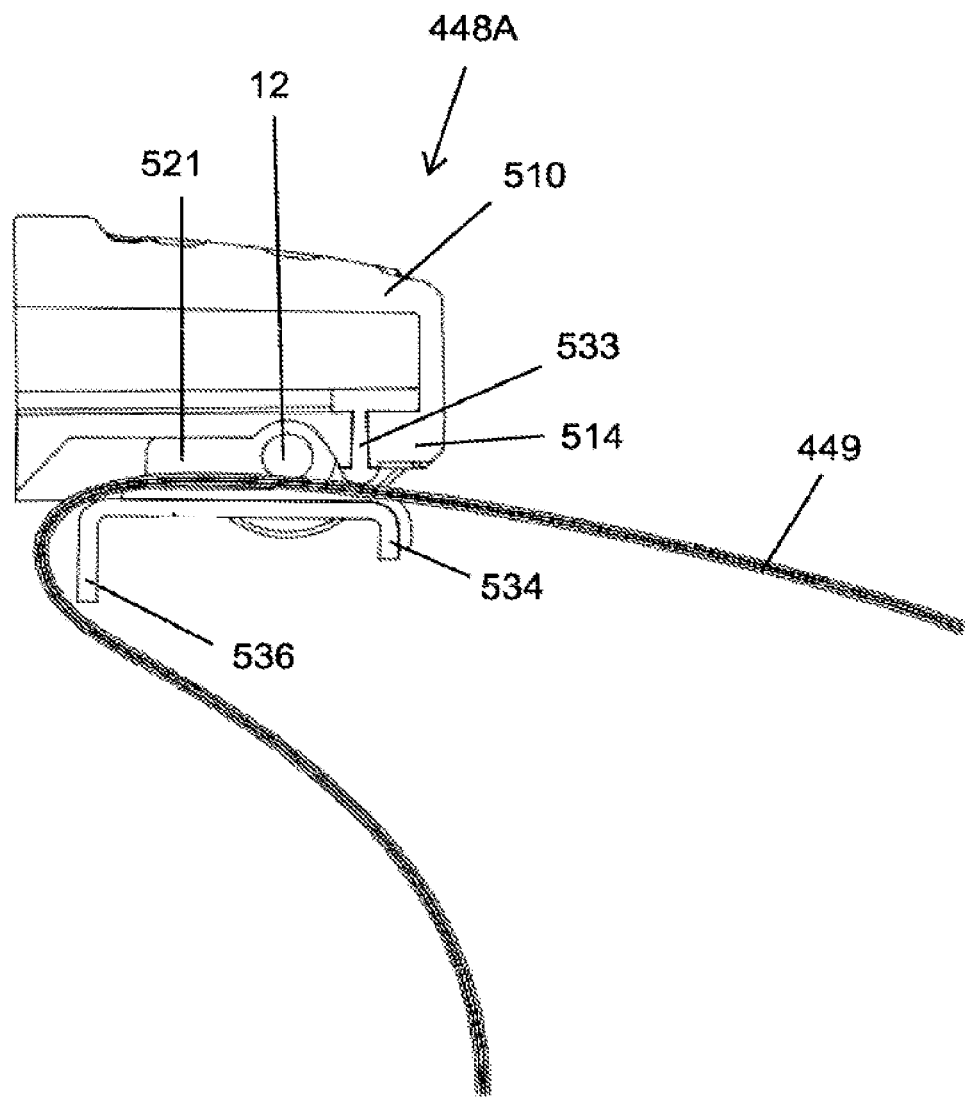
FIG. 32A is a cross sectional view of a portion of the constricting device of FIG. 24, showing the rocker in an unpivoted position.
Figure 32B:
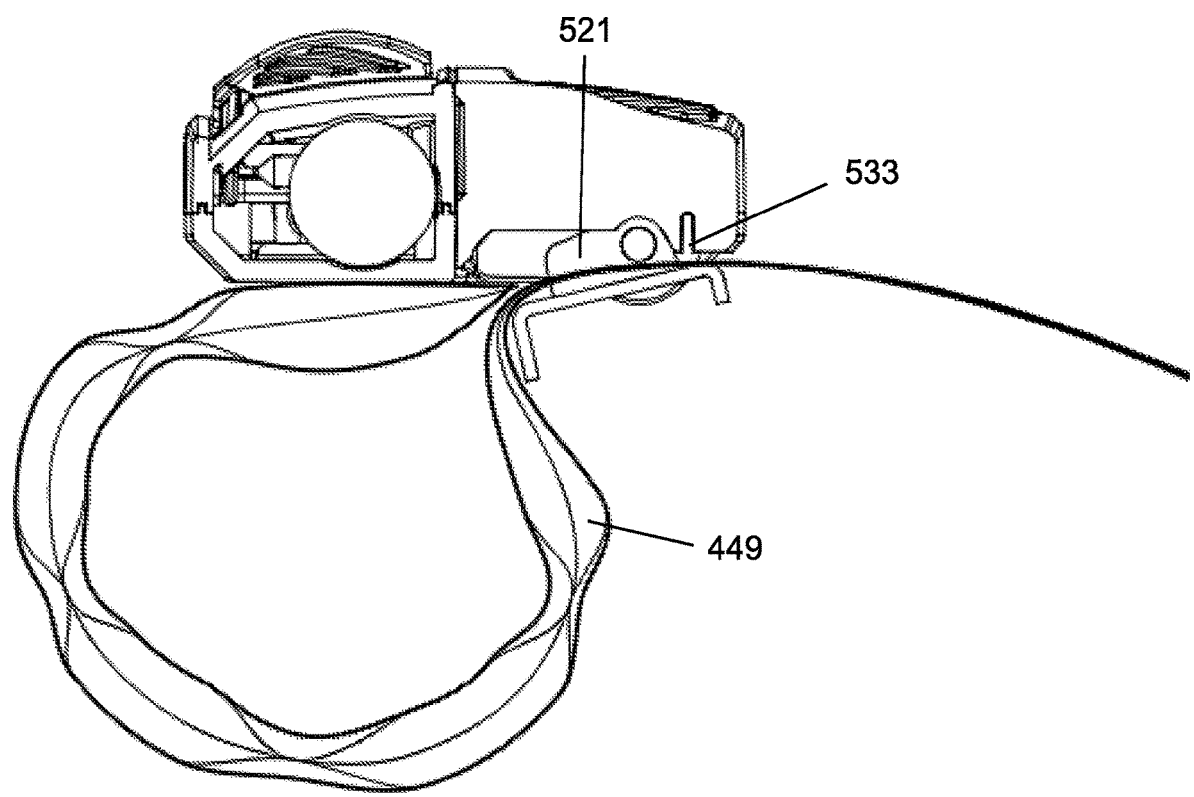
FIG. 32B is a cross sectional view of the tourniquet of FIG. 24, showing the rocker in a pivoted position and the circumferentially extending strap external to the gas flow control assembly and constricting device in perspective view to illustrate the weld lines.
Figure 33:
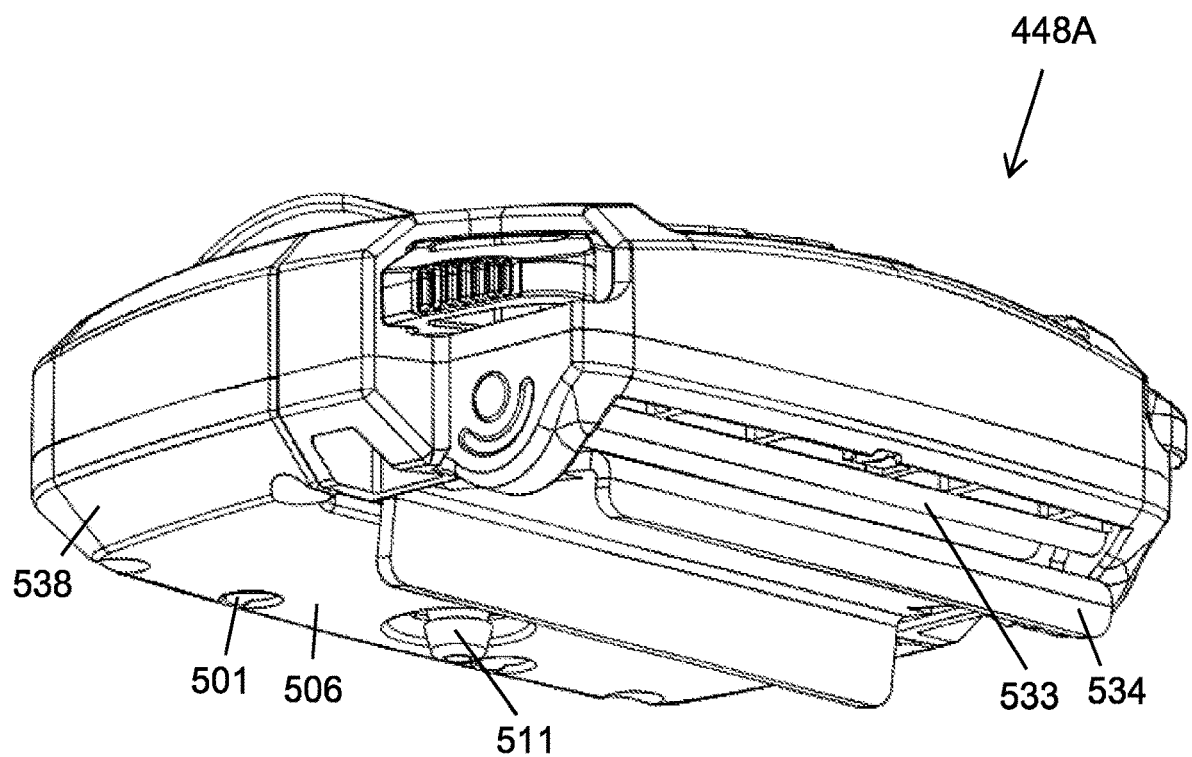
FIG. 33 is a perspective view from the side and bottom of the tourniquet of FIG. 24 when the strap is removed, showing an embodiment of the constricting device.

Reference is now made to FIG. 32A, which illustrates a cross sectional view of a portion of constricting device 448A. Housing member 510 and rocker 521 are configured similarly to, and have a similar function as, their counterparts of FIG. 9, with the exception of the addition of sealing element 533. The distance from axle 12 by which rocker 521 is pivotally displaceable to proximal leg 534 is significantly shorter than the distance to distal leg 536. Distal leg 536 may be significantly longer than proximal leg 534. Also the sidewalls 514 of housing member 510 are formed with a thin interspace, within which longitudinally extending external sealing element 533 is secured. External sealing element 533 is also shown in FIGS. 32B and 33. When rocker 521 is rotated in response to contact made with the wounded limb and to a tensile force applied onto inflatable strap 449 as shown in FIG. 32B, a clamping force is applied onto the strap. External sealing element 533 positioned at the clamping edge, which is preferably semi-rigid, for example having a Shore index of 70, complements the clamping force to prevent the pressurized gas from flowing to the free end of strap 449. Thus the free end of the strap is uninflated, so as to be more comfortable to the subject and to be less prone to puncture.

Figure 34:
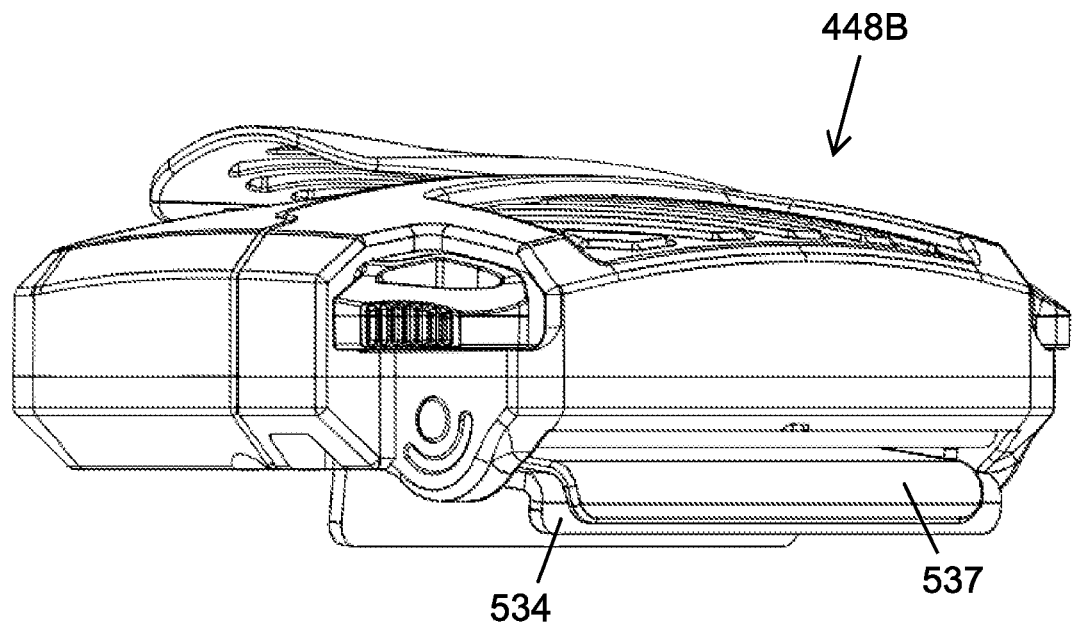
FIG. 34 is a perspective view from the side of the tourniquet of FIG. 24 when the strap is removed, showing another embodiment of the constricting device.

FIG. 34 illustrates a constricting device 448B configured with an external sealing element 537 attached to proximal leg 534 of the rocker.

Figure 35:
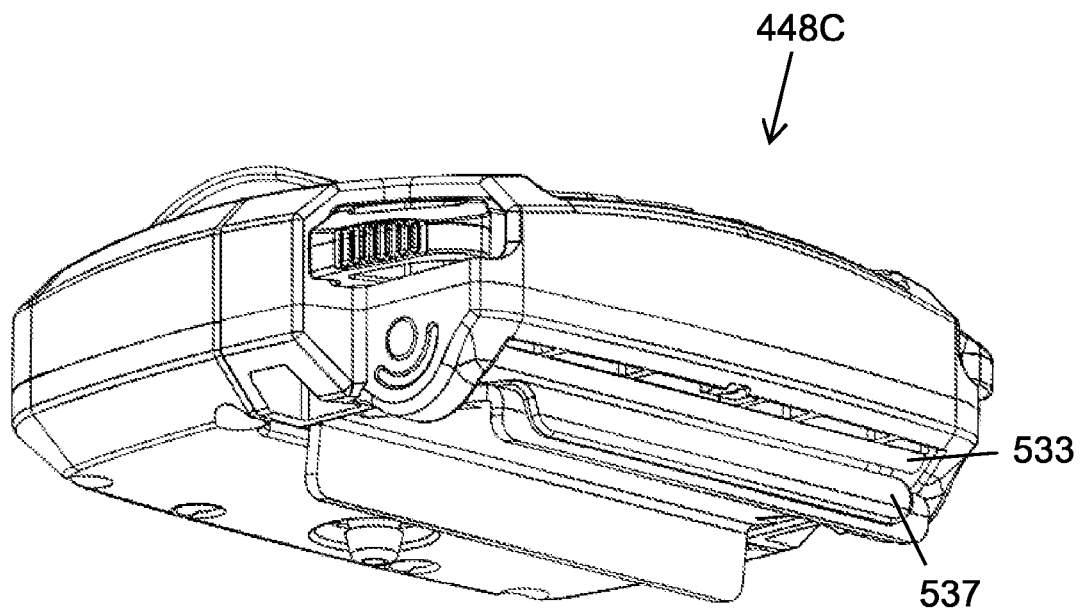
FIG. 35 is a perspective view from the side and bottom of the tourniquet of FIG. 24 when the strap is removed, showing another embodiment of the constricting device.

FIG. 35 illustrates a constricting device 448C configured with both external sealing element 533 and external sealing element 537.

The tourniquet of FIG. 32B, for example, is well suited for combat implementations and for a small-sized tourniquet that can be compactly stored in a soldier's backpack or other piece of storage equipment.

The following are some of the advantageous features of such a small-sized tourniquet:

i. Small Gas Cartridge—The gas cartridge has a volume ranging from 3-7 ml, smaller than the standard volume of 7 ml. The relatively small sized gas cartridge is completely insertable within the gas flow control assembly without protruding outwardly therefrom to prevent damage to the gas cartridge of inadvertent detachment from the gas flow control assembly, a significant advantage in terms of reliability and safety.

ii. Environmental Adaptability-Utilization of a noble gas, such as nitrogen or argon, or a refrigerant gas, which is stored in the gas cartridge in a gaseous state without risk of freezing, allows the pneumatic tourniquet to operate in a wide temperature range of −40° C. to +70° C. The tourniquet is also operable in different environments, such as on land, in the sky or underwater, since it is not influenced by atmospheric pressure.

iii. Activation—The actuator, whether the activation handle or button, has sufficient structural strength to transmit a high-magnitude activation force that causes the pressurized gas to become discharged from the gas cartridge. The structure of the activation handle facilitates simple and intuitive operation, and accordingly hemorrhage suppression may be achieved within only a few seconds.

iv. Inflatable Strap of Two Widths and Interconnected Cells—The unique strap configuration has a smaller width and smaller interior volume than prior art inflatable straps. The wide-width section enables a reduction in the force needed to achieve hemorrhage suppression, and the narrow-width section configured with the interconnected cells allows a smaller volume of pressurized gas to be utilized relative to an inflatable without interconnected cells. The strap is able to be applied to both very small limbs without injury by virtue of the wide-width section which will press on the limb when inflated and also to very large limbs, for example having a circumference of 85 cm, by virtue of the long and narrow-width section.

V. Automatic Pressure Relief Valve—The entire volume of pressurized gas retained in the gas cartridge need not be utilized when the strap is inflated to a constant pre-set pressure. When a predetermined high pressure in the strap interior is achieved, the pressure relief valve will cause some gas from the strap interior to be discharged to the atmosphere to ensure that the strap interior pressure will be reduced to the pre-set pressure. In some embodiments, the pressure relief valve generates an audible reaction, such as a hissing sound, to indicate to the user when to terminate the strap inflation.

vi. Buckle Connecting Gas Flow Control Assembly and Constricting Device—The prongs extending laterally from the gas flow control assembly and insertable in the socket of the non-pivoting constricting device facilitate a simple and intuitive connection that is resistant to high pressures and prevents unwanted detachment.

vii. Constricting Device—The constricting device enables smooth displacement of the strap, and also one-handed manipulation of the strap to facilitate self-deployment of the strap.

While some embodiments of the invention have been described by way of illustration, it will be apparent that the invention can be carried out with many modifications, variations and adaptations, and with the use of numerous equivalents or alternative solutions that are within the scope of persons skilled in the art, without exceeding the scope of the claims.

The invention claimed is:

1. A pneumatic tourniquet, comprising:
   a) an inflatable strap adapted to receive pressurized gas and to be wrapped around a wounded limb to provide a desired hemorrhage suppressing force;
   b) a flexible sealing element; and
   c) a constricting device cooperating with a free end of said strap in such a way that said free end is unrestrainably displaceable within said constricting device until being clamped thereby when said strap is sufficiently tensioned to transmit the hemorrhage suppressing force, wherein said constricting device comprises a housing member and a rocker rotatably mounted onto, and within, said housing member by a longitudinally extending axle, said rocker being configured to be angularly displaced about said axle until a surface of said rocker is set in clamping relation with a clamping edge of said housing member while said strap is interposed between said rocker surface and said clamping edge, in response to a force applied by the wounded limb onto said rocker when said strap is sufficiently tensioned,
   wherein a clamping force applied by said rocker surface and said clamping edge onto said sealing element prevents flow of the pressurized gas from a circumferential pressure applying section of said strap which is wrapped around the wounded limb to said free end, causing said strap free end to be considerably thinner than said circumferential pressure applying section;
   d) a casing which contains a puncture unit housing with which a gas cartridge filled with pressurized gas is coupled, a puncture pin that terminates with a pointed end, and an outlet port; and
   e) means external to the casing for drivingly contacting said puncture pin by an amplified activation force to an inwardly displaced position at which the pointed end of said puncture pin punctures a puncturable cover normally sealing said gas cartridge, causing the pressurized gas to be discharged from the gas cartridge and flow via said outlet port to an interior of the inflatable strap.

2. The pneumatic tourniquet according to claim 1, wherein the strap is configured with first and second sections of different widths, wherein said second section is a circumferential pressure applying section which is narrower and longer than said first section and is adapted to be wrapped around the wounded limb in order to apply circumferential pressure and to suppress hemorrhaging, and said first section is wrappable around at least most of the wounded limb to facilitate substantially even distribution of pressure applied to a surface of the wounded limb and transmission of the desired hemorrhage suppressing force to the wounded limb via said second section.

3. The pneumatic tourniquet according to claim 2, wherein the first and second sections are made of different materials each of which having a different degree of flexibility, such that the second section becomes narrower and longer than the first section following inflation of the strap with the pressurized gas.

4. The tourniquet according to claim 2, wherein the strap is configured with a plurality of serially interconnected cells and with a neck portion that extends between two adjacent cells, to facilitate flow of the pressurized gas between one cell to another.

5. The pneumatic tourniquet according to claim 1, further comprising a member to which the strap is securable, and one or more elements movably connected to the strap-securable member and to the constricting device by which the constricting device is reorientable relative to the strap-securable member even when the strap is removed from the strap-securable member.

6. The pneumatic tourniquet according to claim 5, wherein the strap-securable member is a casing with which a gas cartridge filled with pressurized gas is coupleable therewithin and which is configured with an outlet port, a longitudinally displaceable force transmitting element, and means external to the casing for drivingly contacting said force transmitting element by an amplified activation force to forcefully contact and open at least a portion of an occluding element normally sealing said gas cartridge, causing the pressurized gas to be discharged from said gas cartridge and flow via said outlet port to a strap interior to provide the desired hemorrhage suppressing force.

7. The pneumatic tourniquet according to claim 6, wherein the force transmitting element is a puncture pin that terminates with a pointed end, or is an activation piston configured to cooperate with a valve stem associated with the gas cartridge.

8. The pneumatic tourniquet according to claim 1, wherein the sealing element is external to the strap.

9. The pneumatic tourniquet according to claim 1, wherein the external means comprises:
  a) a pivotable activation handle configured with a wide-area, substantially planar user-manipulatable surface having a width greater than 60% of the width of the casing;
  b) a laterally extending beam which is rotatably mounted in corresponding seats provided with said casing to define an axis of rotation of said activation handle; and
  c) a cam which is fixedly connected to the beam and is in drivable proximity with said puncture pin,
    wherein a ratio of a longitudinal length of said user-manipulatable surface, extending to a line coinciding with the beam and the axis of rotation, to the longitudinal length of the cam from the axis of rotation ranges from 16-22:1,
    wherein, upon pivoted displacement of said activation handle about its axis of rotation, an amplified activation force provided by said ratio is transmitted by said cam that drivingly contacts said puncture pin to forcefully contact and open at least a portion of said puncturable cover causing the pressurized gas to be discharged from said gas cartridge and flow via said outlet port to the interior of the inflatable strap.

10. The pneumatic tourniquet according to claim 6, wherein the external means comprises:
  a) a pivotable activation handle configured with a wide-area, substantially planar user-manipulatable surface having a width greater than 60% of the width of the casing;
  b) a laterally extending beam which is rotatably mounted in corresponding seats provided with said casing to define an axis of rotation of said activation handle; and
  c) a cam which is fixedly connected to the beam and is in drivable proximity with said puncture pin,
    wherein a ratio of a longitudinal length of said user-manipulatable surface, extending to a line coinciding with the beam and the axis of rotation, to the longitudinal length of the cam from the axis of rotation ranges from 16-22:1,
    wherein, upon pivoted displacement of said activation handle about its axis of rotation, an amplified activation force provided by said ratio is transmitted by said cam that drivingly contacts said force transmitting element to forcefully contact and open at least a portion of said occluding element causing the pressurized gas to be discharged from said gas cartridge and flow via said outlet port to an interior of the inflatable strap.

11. The pneumatic tourniquet according to claim 10, wherein the occluding element is a puncturable cover and the force transmitting element is a puncture pin that terminates with a pointed end that is drivable to an inwardly displaced position at which the pointed end punctures the puncturable cover.

12. The pneumatic tourniquet according to claim 10, wherein the force transmitting element is an activation piston configured to cooperate with a valve stem associated with the gas cartridge.

13. The pneumatic tourniquet according to claim 1, further comprising:
  a) a housing member, which is configured with an internal cavity;
  b) a shell connected to the housing member and formed with a plurality of parallel passageways; and
  c) a pressure regulating unit configured with an inlet that passes through the housing member for receiving pressurized gas upon demand; and
  d) a piston axially and differentially displaceable within the internal cavity to define at a distal end thereof a supply chamber in fluid communication with atmospheric air and, at a proximal end thereof, a regulating chamber adjoining said shell, said regulating chamber being in fluid communication with said inlet by a tube passing through an entire thickness of said piston and with the interior of the strap via one of said passageways.

14. The pneumatic tourniquet according to claim 13, further comprising:
  a) the housing member, which is configured with the inlet for receiving pressurized gas upon demand;
  b) the tube, which is hollow so as to be in fluid communication with the inlet and has an outer diameter of less than 2.5 mm and a distal end with an unsmooth finish;
  c) the piston which is intermediately bored and connected to, and which has an outer diameter significantly greater than, the tube; and
  d) a fixed sealing element,
    wherein, following flow of the pressurized gas into said regulating chamber through the tube, the piston is caused to be distally displaced by a pressure differential between the pressure in said regulating chamber and in said supply chamber until the distal end of the tube is occluded by said sealing element, to prevent additional inflow of the pressurized gas.

15. The pneumatic tourniquet according to claim 13, further comprising a manual pressure release initiator axially displaceable within another one of said passageways that is in fluid communication with said regulating chamber and with atmospheric air, which, when distally displaced to a fullest extent, contacts said piston to occlude said tube and to prevent additional inflow of the pressurized gas to said regulating chamber, and also provides a clearance relative to a wall of said another passageway to cause egress of the pressurized gas received in said regulating chamber to the atmospheric air and to selectively reduce the pressure of the fluid within said strap interior.

16. The pneumatic tourniquet according to claim 1, wherein the puncture pin has, for at least one region thereof, a solid shaft of a uniform diameter that is cut at an angle to define a planar surface having a sharp peripheral edge configured such that the pointed end is coincident with the peripheral edge and with an outer surface of the shaft, producing an unsealed passageway adjoining the shaft outer surface along which the pressurized gas is discharged from the gas cartridge following puncturing of the cover by the pointed end.

* * * * *